US012697462B2

(12) United States Patent (10) Patent No.: US 12,697,462 B2
Shi (45) Date of Patent: Aug. 4, 2026

(54) SLEEP AID APPARATUS AND CONTROL THEREOF

(71) Applicant: KONINKLIJKE PHILIPS N.V., Eindhoven (NL)

(72) Inventor: Jun Shi, Shanghai (CN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 520 days.

(21) Appl. No.: 18/214,233

(22) Filed: Jun. 26, 2023

(65) Prior Publication Data

US 2024/0001069 A1 Jan. 4, 2024

(30) Foreign Application Priority Data

Jun. 30, 2022 (WO) ................ PCT/CN2022/102625
Sep. 9, 2022 (EP) ..................................... 22194884

(51) Int. Cl.
*A61M 21/02* (2006.01)
*A61M 21/00* (2006.01)

(52) U.S. Cl.
CPC ..... *A61M 21/02* (2013.01); *A61M 2021/0022* (2013.01); *A61M 2230/06* (2013.01)

(58) Field of Classification Search
CPC .......... A61M 21/02; A61M 2021/0022; A61M 2230/06; A61M 2021/0088; A61M 2205/07; A61M 2205/3303; A61M 2205/50; A61M 2205/582; A61M 2230/04; A61M 2230/42; A61B 5/02405; A61B 5/0816; A61B 5/6887; A61B 5/0205
See application file for complete search history.

(56) References Cited

U.S. PATENT DOCUMENTS 9,649,470 B2 5/2017 Vogt et al.
9,861,817 B2 * 1/2018 Cho ..................... A61N 1/3601
11,052,222 B2 7/2021 Engel et al.
(Continued)

OTHER PUBLICATIONS

Tsai et al., "Efficacy of paced breathing for insomnia: enhances vagal activity and improves sleep quality", Psychophysiology. Mar. 2015; 54(3), pp. 388-396.

(Continued)

*Primary Examiner* — Bo Joseph Peng
(74) *Attorney, Agent, or Firm* — Brynne Corcoran

(57) ABSTRACT

Improved means for guiding a user in paced breathing for sleep induction. A processing device controls generating of a cyclically patterned user-perceptible stimulus to guide a user in pacing their breathing. In some embodiments, means are included for aligning a phase of the cyclically patterned first user-perceptible stimulus with a phase of the user's breathing cycle. In some embodiments, means are included for aligning an initial (i.e. starting) phase of the cyclically patterned first user-perceptible stimulus with a phase of the user's breathing cycle at the moment of starting. In some embodiments, means are included for detecting asynchrony between the phase of the guiding stimulus and the phase of the user's breathing cycle, and a response is performed based on the detected asynchrony. The response may be to communicate a synchronization status to the user via a second user-perceptible stimulus or output. The response may be to take steps to correct any asynchrony.

15 Claims, 8 Drawing Sheets

(56) References Cited

U.S. PATENT DOCUMENTS

| | | | |
|---|---|---|---|
| 2005/0039745 A1* | 2/2005 | Stahmann | A61B 5/4818 |
| | | | 128/204.18 |
| 2005/0043772 A1* | 2/2005 | Stahmann | A61N 1/36514 |
| | | | 607/42 |
| 2005/0061315 A1* | 3/2005 | Lee | A61B 5/4818 |
| | | | 128/204.23 |
| 2005/0209504 A1 | 9/2005 | Elliott | |
| 2012/0277521 A1* | 11/2012 | Chamberlin | A61M 21/02 |
| | | | 600/26 |
| 2015/0367097 A1 | 12/2015 | Gavish | |
| 2020/0338303 A1 | 10/2020 | Engel et al. | |
| 2022/0152340 A1 | 5/2022 | De Goeij et al. | |
| 2022/0175309 A1 | 6/2022 | Vardas et al. | |
| 2022/0233860 A1 | 7/2022 | Hamner et al. | |

OTHER PUBLICATIONS

Laborde et al., "Influence of a 30-Day Slow-Paced Breathing Intervention Compared to Social Media Use on Subjective Sleep Quality and Cardiac Vagal Activity", J Clin Med. Feb. 2019; 8(2): 193.

Marentakis et al., "Using Breath-like Cues for Guided Breathing", Extended Abstracts of the 2021 Chi Conference on Human Factors in Computing Systems, Yokohama, Japan, May 8, 2021, pp. 1-7.

* cited by examiner

112

112

124

132

112

122

142

132

142

122

SLEEP AID APPARATUS AND CONTROL THEREOF

This application claims the benefit of International Application No. PCT/CN2022/102625 filed Jun. 30, 2022, and European Application No. 22194884.7, filed on Sep. 9, 2022. These applications are hereby incorporated by reference herein.

FIELD OF THE INVENTION

This invention relates to the field of sleep aid devices, for example sleep aid devices for aiding sleep induction.

BACKGROUND OF THE INVENTION

One-third of the general adult population reports symptoms of insomnia. It is a major public health concern and may lead to loss of concentration, memory, and performance, as well as physical disease. Current pharmaceutical treatments can be expensive, unhealthy, and habit-inducing. Latest studies, referenced below, have showed that slow paced breathing practiced by an individual at the time of attempting to sleep helps to improve sleep onset and sleep quality. This has led to development of products aimed at inciting individuals to follow particular (slow) breathing rhythms. This concept generally is known as paced-breathing. Various solutions exist to help individuals with paced breathing such as paced breathing Apps, paced breathing videos, and other means.

This new area of development opens new possibilities for further improvement and optimization, and for new improved solutions to the general problem.

Reference is made to: H J Tsai, Efficacy of paced breathing for insomnia: enhances vagal activity and improves sleep quality, Psychophysiology. 2015 March; 54(3):388-96.

Reference is made to: Sylvain Laborde, Influence of a 30-Day Slow-Paced Breathing Intervention Compared to Social Media Use on Subjective Sleep Quality and Cardiac Vagal Activity, J Clin Med. 2019 February; 8(2): 193.

SUMMARY OF THE INVENTION

This disclosure outlines a number of developments devised by the inventor in the area of paced breathing aimed at addressing one or more shortcomings in the existing state of the art which have been newly recognized by the inventors.

Within current solutions, generally a sensory stimulus is generated which is rhythmically patterned with a certain frequency, and wherein the user is instructed to adjust the pace of their breathing to follow the pace of the stimulus. One shortcoming identified by the inventors is that the phase of the guiding stimulus may mismatch with the user's respiration phase. The phase might typically be fixed when the device is powered on and not aligned with the user's inhalation phase. Users therefore need to suddenly adjust their inhalation and exhalation phase to get in sync with the phase of periodic stimulus, for example by cutting short a breath to start a new breath or holding their breath longer than would otherwise be comfortable. This causes the user to feel discomforted and nervous, and indeed prompts an involuntary physiological response of anxiety which is contrary to the intended aim of relaxation for sleep. Also, in some instances, the user may follow the sensory stimulus in the reverse phase. This does not cause an issue for a stimulus cycle which has a 1:1 inhalation to exhalation phase length, case but will decrease the performance for the paced breathing when the inhalation to exhalation phase ratio is not 1:1, for example, 1:2.

Another deficiency in the current state of the art identified by the inventors is that known solutions employ a standardized frequency or frequency pattern for the guiding stimulus. However, the breathing pace best associated with sleep onset actually varies from person to person, and even for a single individual, varies over time. It is associated with certain physiological parameters of the user. Therefore a fixed frequency paced breathing guide is non-optimal.

Another deficiency in the current state of the art is that the particular sensory modalities currently employed for communicating the breathing guidance are somewhat inapt for the general aim of inducing relaxation and sleep. For example, they typically rely on periodic acoustic stimuli. However, these can in fact be jarring and stress-inducing, and, if maintained throughout sleep, can lead to disturbed sleep. A better way of communicating the target breathing pattern would therefore be of value.

Outlined below is a summary of concepts devised by the inventors aimed at addressing one of more of the above identified deficiencies in the current state of the art.

The invention is defined by the claims.

According to a first aspect of the invention, there is provided a processing device for a sleep-aid apparatus, the sleep aid apparatus comprising one or more stimulus generators operable to generate one or more user-perceptible stimuli with one or more sensory modalities, and the sleep aid apparatus further comprising a physiological sensor. The processing device can be provided by itself, for use with the sleep-aid apparatus, e.g. for use in controlling the sleep aid apparatus. Also, in a second aspect of the invention is the sleep aid apparatus comprising the processing device. Also, in a third aspect of the invention is a system comprising the sleep aid apparatus and the processing device in combination but separate, for example with the processing device embodied in a mobile computing device such as a smartphone. These options also apply for all of the other aspects of the invention.

The processing device is adapted to monitor a respiration phase of the user based on processing of an input sensor signal from the physiological sensor.

The processing device is further adapted to control generation (by the one or more stimulus generators) of a first user-perceptible stimulus which is cyclically patterned for guiding a user in matching a pacing of their breathing to a cycle phase and cycle frequency of the first user-perceptible stimulus. The cyclical patterning means for example a cyclical patterning of an intensity of the relevant stimulus.

In some embodiments, the processing device is further adapted to configure a cycle phase of the first user-perceptible stimulus based on the user respiration phase. The processing device may for example be adapted to configure an initial or starting cycle phase of the first user-perceptible stimulus based on the user respiration phase. For example, the processing device may be adapted to set an initial or starting cycle phase of the first user perceptible stimulus to match a cycle phase of the user respiration cycle. For example, the processing device may be adapted to perform a starting routine in which, using the sensor signal from the physiological sensor, a respiration phase of the user is monitored over one or more respiration cycles. Following this, the generation of the first user-perceptible stimulus may be started such that, upon starting, a cycle phase of the first user-perceptible stimulus matches a respiration phase of the user.

Additionally or alternatively, in some embodiments, the processing device is further adapted to determine a synchronization status between the cycle phase of the first user-perceptible stimulus and the user respiration phase. The synchronization status means for example an indication of a degree of phase alignment between the cycle phase of the first user-perceptible stimulus and the user respiration phase.

In some embodiments, the processing device is further adapted to perform a response action dependent upon the synchronization status. In some embodiments, the response action is for improving/increasing synchronization between the cycle phase of the first user-perceptible stimulus and the user respiration phase.

By determining the degree of synchronization between the phase of the paced breathing guiding stimulus and the current phase of the user's breath, steps can be taken to aid in reducing any misalignment therebetween. This therefore helps to mitigate the problem mentioned above wherein a user feels anxiety and stress due to the mismatch between their current breathing phase and the stimulus phase.

It is to be noted that there is a distinction between the stimulus frequency and the stimulus phase. The user's breathing frequency could in fact be perfectly matched to the guiding the stimulus frequency, but their breath is out of phase with the stimulus. This triggers a stress response which is not conducive to the relaxation state needed for sleep. Therefore there is value in providing a solution which can help ameliorate phase disparities, even entirely independently of any control or adjustments to the underlying frequency or period of the first user-perceptible stimulus (although solutions to address frequency are also proposed further below and could be combined with the phase-related solutions).

It is also noted that in the context of this disclosure, the terms breathing cycle and respiration cycle are used synonymously. Therefore reference to respiration phase or frequency and reference to breathing phase or frequency may be taken as references to the same thing.

It is also noted that, in the context of this disclosure, the terms cycle frequency and cycle period, applied in respect of the first user perceptible stimulus means the frequency of repetition of each cycle of the cyclical pattern embodied by the first user-perceptible stimulus. This might be a smooth, sinusoidal pattern, or could be a differently shaped pattern, for example being skewed for guiding a longer exhalation than inhalation. For example, each cycle of the cyclically patterned first user-perceptible stimulus might include an inhalation phase portion, and an exhalation phase portion, and the durations of the inhalation and exhalation phase portions might be different to one another. In other words, a ratio between an inhalation and exhalation phase portion duration may not be 1:1. For example it could be 1:2. A longer exhalation cycle is helpful to modulate the parasympathetic nerve system, and is good for relaxation. In all cases, the stimulus will exhibit a repeating 'unit' or 'cycle' of the pattern, and the frequency means the frequency of repetition of this unit or cycle, and the period means the time duration spanned by one instance of this unit or cycle of the pattern.

In some embodiments, the aforementioned response action may be for guiding a user in improving the synchronization status. Additionally or alternatively, the response action may be for directly adjusting the stimulus so as to improve the synchronization status.

In some embodiments, the processing device is adapted to perform one or more adjustments of the cycle phase of the first user-perceptible stimulus so as to align it with a current respiration phase of the user. In other words, the aforementioned response action comprises performing the said one or more adjustments of the cycle phase of the first user-perceptible stimulus.

In other words, in this set of embodiments, the processing device corrects a phase-misalignment between the stimulus phase and the user breathing phase. Thus, stimulation starts synchronized with the inhalation phase or exhalation phase. The phase is synchronized automatically with the user's breathing phase.

As mentioned above, in some embodiments, controlling generation of the first user-perceptible stimulus comprises controlling a cycle frequency of the first user-perceptible stimulus.

In some embodiments, the one or more adjustments of the cycle phase of the first user-perceptible stimulus are performed independently of the control of the cycle frequency of the stimulus. In other words the adjustments to the cycle phase of the first user-perceptible stimulus are done without changing the frequency of the first user-perceptible stimulus (without changing the aforementioned control of the frequency). In other words, in-between said adjustments, the cycle frequency is controlled independently in accordance with a (possible independently adjustable) cycle frequency parameter.

In some embodiments, the cycle phase alone may be adjusted, for example on a recurrent basis, so that as discrepancies between the user-perceptible stimulus cycle and the breathing cycle of the user are detected, adjustments are made to the phase to make it match the user's phase, but the underlying frequency of the user-perceptible stimulus is maintained. In other words, it is proposed to, on a single occasion, or intermittently, distort the user-perceptible stimulus cycle to correct or compensate for phase disparities that have emerged between it and the user's breathing pace, but to maintain the underlying patterning of the signal. So discrete adjustments or compensations of phase or cycle period of the stimulus can be applied at intermittent time points, but then, in-between these adjustments, the stimulus cycle is allowed to proceed in accordance with its original frequency. The adjustment could comprise a phase translation of the stimulus cycle, i.e. jumping to a different part of the cycle. The adjustment could comprise temporarily speeding up or slowing the stimulus pacing to 'catch up' with the user breathing pace, before then returning to the original frequency. The adjustment could comprise cutting short a current cycle, or extending a current cycle to achieve the phase alignment. The skilled person will recognize there are multiple particular means for achieving the effect.

In some embodiments, the aforementioned one or more adjustments are performed at recurrent/repeating time points.

In some embodiments, the performing the one or more adjustments comprises, at each said repeating time point: detecting any disparity between the cycle phase of the first user perceptible stimulus and the respiration phase of the user; and adjusting the cycle phase of the first user-perceptible stimulus such that it matches the respiration phase of the user.

During periods in-between said repeating time points, the first user-perceptible stimulus may be generated with a fixed or independently controlled cycle frequency.

In some embodiments, processing device is adapted to control the cycle frequency of the first user-perceptible stimulus in dependence upon a physiological parameter determined from processing of the physiological sensor signal.

In some embodiments, the processing device is further adapted to process the physiological sensor signal to determine a heart rate variability (HRV) amplitude of the user, and set a frequency of the first user-perceptible stimulus in dependence thereon.

In some embodiments, the processing device is further adapted to implement a calibration procedure for setting the cycle frequency of the first user-perceptible stimulus, the calibration procedure comprising a series of epochs, and wherein:

the cycle frequency of the first user-perceptible stimulus is set at a different respective value in each respective epoch;

during each epoch, the physiological sensor signal is processed to determine an HRV of the user; and the cycle frequency of the first user-perceptible stimulus is set equal to the cycle frequency during the calibration procedure which coincided with a highest measured HRV.

Within the technical field, this frequency which stimulates a highest measured HRV amplitude is sometimes referred to as the HRV resonant frequency.

The HRV resonant frequency corresponds to a cycle frequency of the first user-perceptible stimulus which coincides with a highest measured HRV as measured over a plurality of epochs, within each of which a cycle frequency of the first user-perceptible stimulus was set to a different value.

The peak HRV is known to be associated with the best state for inducement of relaxation and sleep. Therefore it is proposed to measure the breathing pace which stimulates the peak HRV for the particular user of the device and then to set the cycle frequency of the first user-perceptible stimulus to match this pace. This can be achieved by directly measuring a physiological parameter of the user from which heart rate is derivable and then using the heart rate signal to derive HRV over a series of epochs in which the stimulus frequency is varied.

The physiological sensor could be a PPG sensor in some embodiments.

To address the problem outlined above that the stimuli used currently in the art are jarring or stress inducing for the user, the inventors have devised a new approach to generating the stimulus.

In some embodiments, the first user-perceptible stimulus is a tactile or haptic stimulus.

In some embodiments, the first user-perceptible stimulus comprises a cyclical motion induced by an actuation mechanism. A movement stimulus has not previously been considered, and is highly advantageous. Movement does not arouse the senses in the way that an acoustic or visual stimulus does, or even in the way that a vibratory stimulus might. It is a more gentle stimulus, and naturally congruous with the action of breathing itself which is manifests a motion pattern.

In some embodiments for example, the cyclical motion comprises cyclical expansion and contraction of at least a part of an article adapted for being in contact with a user during use.

In some embodiments, the actuation mechanism is a pneumatic actuation mechanism, and wherein the first user-perceptible stimulus comprises cyclical inflation and deflation of a bladder integrated inside said article.

As will be discussed in more detail below, in some embodiments, the article may be a pillow or cushion which the user can hold against their body which expands and contracts cyclically to provide the cyclical pattern.

In a fourth aspect of the invention, there may be a sleep aid apparatus comprising: one or more stimulus generators operable to generate one or more user-perceptible stimuli with one or more sensory modalities; a physiological sensor; and a processing device, wherein the sleep aid apparatus comprises an article for making physical contact with a user during sleep induction, and wherein the physiological sensor is integrated in the article, and wherein the first user-perceptible stimulus comprises a cyclical motion of at least a part of the article, for example a cyclical expansion and contraction of at least a part of the article, and the article including actuation means for implementing said cyclical motion.

Returning to the problem of synchronization between the phase of the stimulus and the respiration phase, a further solution is proposed below.

In some embodiments, the processing device is adapted to control generation of a second user-perceptible stimulus indicative of the synchronization status between the cycle phase of the first user-perceptible stimulus and the user breathing phase. In other words, the aforementioned response action may comprise said control of a second user-perceptible stimulus. By communicating to the user an indication of the synchronization status, this assists the user in bringing their breathing more smoothly into sync with the first stimulus phase.

This provides feedback to user, allowing the user to adjust their breathing if they are un-synchronized to certain level.

In some embodiments, the second user-perceptible stimulus comprises a stimulus which is: continuously generated when the user's breathing phase is synchronized with the cycle phase of the first user-perceptible stimulus; and not generated when the user's breathing phase is non-synchronized with the cycle phase of the first user-perceptible stimulus. This gives a positive reinforcement feedback to guide the user in keeping their breathing phase synchronized with the phase of the first user perceptible stimulus.

In some embodiments, the second user-perceptible stimulus comprises a vibration stimulus.

In some embodiments, when the user's breathing phase is synchronized with the cycle phase of the first user-perceptible stimulus, an amplitude of the vibration is modulated in synchrony with the user's breathing phase. In other words, when the user is correctly synchronized with the guiding (first) stimulus, they are given positive reinforcement in the form of a cyclical second user-perceptible stimulus which follows their breathing pace.

In some embodiments, the second user-perceptible stimulus comprises a modulation of a baseline or offset of the cyclical pattern of the first user-perceptible stimulus.

In other words, the proposal in this set of embodiments is to use a (further) modulation applied to the first stimulus (i.e. the stimulus for guiding the breathing pace) to give the user the synchronization status feedback. It is proposed to modulate the baseline intensity of the first user perceptible stimulus.

In a fifth aspect, the invention is a sleep-aid apparatus which comprises: one or more stimulus generators operable to generate one or more user-perceptible stimuli with one or more sensory modalities; a physiological sensor; and a processing arrangement in accordance with any embodiment described in this document, or in accordance with any claim.

In some embodiments, the sleep aid apparatus further comprises an article for making physical contact with a user during sleep induction; and wherein the physiological sensor is integrated in the article.

In some embodiments, the article has a textile surface and/or the article is cushioned at least at its surface.

In some embodiments, the article is a pillow or cushion.

In some embodiments, the article is for holding by a user against their body with one or more hands, e.g. for grasping or hugging by a user, thereby bringing their hand into continuous contact with the device.

In some embodiments, the physiological sensor is arranged so as to have a sensitive area accessible to physical contact at a surface of the article. For example, the sensor may be a PPG sensor.

In some embodiments, said sensitive area of the physiological sensor is covered by a pocket or cover element extending over the sensitive area, the pocket or cover element attached to a surface of the article, and wherein the sensitive area is accessible to physical contact via an opening of the pocket or cover element. For example, this may be a fabric or textile cover element.

In some embodiments, the apparatus further includes a finger placement guide for guiding a user in physical placement of their finger over the sensitive area.

In some embodiments, the finger placement guide provides physical or tactile guidance, for guiding placement of the finger without visual observation by the user.

In some embodiments, the finger placement guide is adapted to releasably hold the finger in place.

In some embodiments, the finger placement guide comprises a band through which a user can insert their finger for holding the finger in place.

Any of the various embodiments of the method outlined above can also be embodied in the form of a method.

Thus, a sixth aspect, the invention provides a sleep-induction method, comprising: monitoring a respiration or breathing phase of the user based on processing of an input physiological sensor signal associated with the user; and generating a first user-perceptible stimulus which is cyclically patterned for guiding a user in matching a pacing of their breathing to a cycle phase of the user-perceptible stimulus. In some embodiments, the method further comprises configuring a cycle phase of the first user-perceptible stimulus based on the user respiration phase. In some embodiments, the method further comprises configuring an initial or starting cycle phase of the first user-perceptible stimulus based on the user respiration phase. Additionally or alternatively, in some embodiments, the method further comprises determining a synchronization status between the cycle phase of the first user-perceptible stimulus and the user breathing phase. In some embodiments, the method further comprises performing a response action dependent upon the synchronization status.

Any of the optional features already outlined above in respect of the processing device can also be embodied as features of the method.

In some embodiments, the method comprises performing one or more adjustments of the cycle phase of the first user-perceptible stimulus so as to align it with a current respiration phase of the user. In other words, the aforementioned response action comprises performing the said one or more adjustments.

In some embodiments, the method comprises further controlling the cycle frequency of the first user-perceptible stimulus in dependence upon a physiological parameter determined from processing of the physiological sensor signal.

In some embodiments, the method further comprises processing the physiological sensor signal to determine a heart rate variability (HRV) of the user, and setting a frequency of the first user-perceptible stimulus in dependence thereon.

In some embodiments, the method comprises implementing a calibration procedure for setting the cycle frequency of the first user-perceptible stimulus, the calibration procedure comprising a series of epochs, and wherein:

the cycle frequency of the first user-perceptible stimulus is set at a different respective value in each respective epoch;

during each epoch, the physiological sensor signal is processed to determine an HRV of the user;

the cycle frequency of the first user-perceptible stimulus is set equal to the cycle frequency during the calibration procedure which coincided with a highest measured HRV.

In some embodiments, the method comprises controlling generation of a second user-perceptible stimulus indicative of a synchronization status between the cycle phase of the first user-perceptible stimulus and the user breathing phase. In other words, the aforementioned response action may comprise said control of a second user-perceptible stimulus. By communicating to the user an indication of the synchronization status, this assists the user in bringing their breathing more smoothly into sync with the first stimulus phase.

In a seventh aspect, the invention is a method for controlling a sleep-aid apparatus, the sleep aid apparatus comprising one or more stimulus generators operable to generate user-perceptible stimuli with one or more sensory modalities to guide a user in matching a pacing of breathing of the user to a cycle frequency of the user-perceptible stimulus, and the sleep aid apparatus further comprising at least one physiological sensor operable to generate sensor data. The method comprises:

receiving the sensor data from the at least one physiological sensor;

determining a respiration phase of the user based the sensor data;

determining a heart rate variability (HRV) of the user based on the sensor data;

providing control signals to the one or more stimulus generators to generate multiple user-perceptible stimuli, each of the multiple user-perceptible stimuli having a different cycle frequency;

determining the heart rate variability for each of the different cycle frequencies;

providing a further control signal to the one or more stimulus generators to generate a first user-perceptible stimulus based on the respiration phase and the determined heart rate variability.

In an embodiment, the method comprises determining a cycle frequency of the different cycle frequencies corresponding to the highest heart rate variability, and providing, after determining the cycle frequency corresponding to the highest heart rate variability, the further control signal based on the cycle frequency corresponding to the highest heart rate variability.

In an embodiment, the method comprises determining a synchronization status between a cycle phase of the first user-perceptible stimulus and the respiration phase of the user, and performing a response action based on the synchronization status, and wherein the response action comprises performing one or more adjustments of the cycle phase of the first user-perceptible stimulus so as to align with a current respiration phase of the user.

In an embodiment, wherein the one or more adjustments are performed at recurrent/repeating time points.

In an embodiment, the method comprises determining a synchronization status between the cycle phase of the first user-perceptible stimulus and the respiration phase of the user, and performing a response action based on the synchronization status, and wherein the response action comprises providing a second control signal to at least one of the stimulus generators to generate of a second user-perceptible stimulus indicative of the synchronization status between the cycle phase of the first user-perceptible stimulus and the breathing phase of the user.

In an embodiment, the second user-perceptible stimulus comprises a stimulus which is:

continuously generated when the respiration phase of the user is synchronized with the cycle phase of the first user-perceptible stimulus; and not generated when the respiration phase of the user is non-synchronized with the cycle phase of the first user-perceptible stimulus.

In an embodiment, the second user-perceptible stimulus comprises a vibration stimulus. The method comprises, when the respiration phase of the user is synchronized with the cycle phase of the first user-perceptible stimulus, modulating an amplitude of the vibration in synchrony with the respiration phase of the user.

In an eight aspect, the invention is a sleep-aid apparatus comprising one or more stimulus generators operable to generate user-perceptible stimuli with one or more sensory modalities; at least one physiological sensor; and a processing device adapted to perform the method in accordance with the seventh aspect.

In an embodiment, the sleep-aid apparatus comprises an article for making physical contact with a user during sleep induction; and the physiological sensor is integrated in the article.

In an embodiment, the article is cushioned at least at a surface of the article.

In an embodiment, the article is a pillow or a cushion.

In an embodiment, the at least one physiological sensor is arranged so as to have a sensitive area accessible to physical contact at a surface of the article, and wherein said sensitive area is covered by a pocket or cover element extending over the sensitive area, wherein the pocket or cover element is attached to a surface of the article, and wherein the sensitive area is accessible to physical contact via an opening of the pocket or cover element.

In an embodiment, the physiological sensor is a PPG sensor.

In an embodiment, the first user-perceptible stimulus is a tactile or haptic stimulus and comprises a cyclical motion induced by an actuation mechanism.

In a ninth aspect, the invention is a computer program product comprising instructions which, when run on a processing device, cause the processing device to perform the method according to the seventh aspect.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
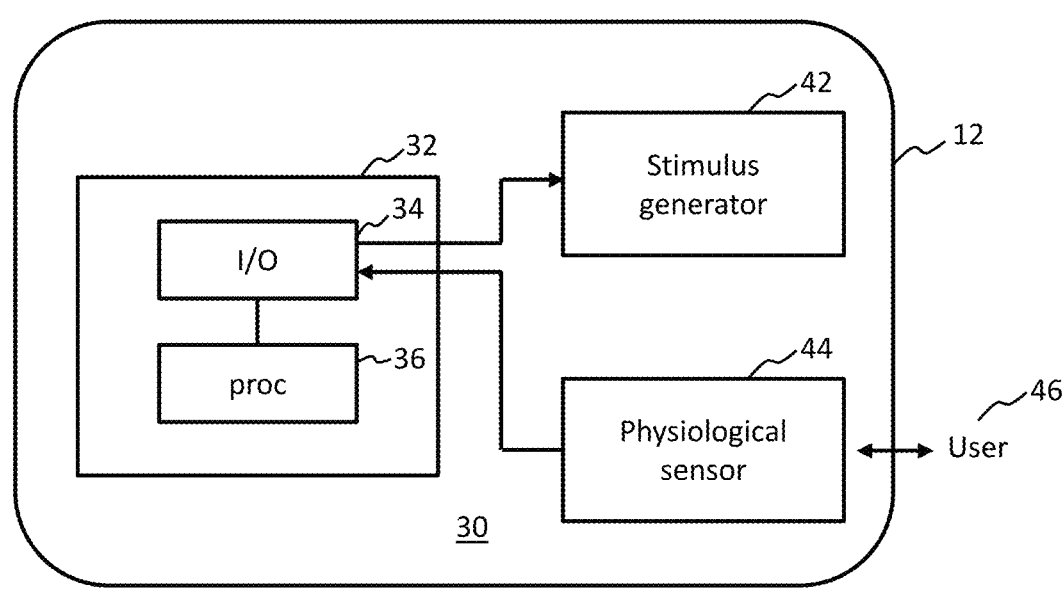
FIG. 1 schematically illustrates components of an example sleep aid apparatus comprising a processing device in accordance with one or more embodiments of the present invention.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides improved means for guiding a user in paced breathing for sleep induction. A processing device controls generating of a cyclically patterned user-perceptible stimulus to guide a user in pacing their breathing. In some embodiments, means are included for aligning a phase of the cyclically patterned first user-perceptible stimulus with a phase of the user's breathing cycle. In some embodiments, means are included for aligning an initial (i.e. starting) phase of the cyclically patterned first user-perceptible stimulus with a phase of the user's breathing cycle at the moment of starting. In some embodiments, means are included for detecting asynchrony between the phase of the guiding stimulus and the phase of the user's breathing cycle, and a response is performed based on the detected asynchrony. The response may be to communicate a synchronization status to the user via a second user-perceptible stimulus or output. The response may be to take steps to correct any asynchrony.

As has been discussed above, in currently known paced breathing devices, while the user is following the correct patterning or frequency of the stimulus, there could arise the case that the phase is mis-aligned or totally inversed. For example, the stimulation might be in the inhalation phase, but the user is in exhalation phase. This is not an issue when the inhalation and exhalation duration ratio is 1:1. However, the inhalation and exhalation ratio for slow paced breathing may not be 1:1, for example it might be 1:1.2, etc. When the phase is inversed, the exercise performance changes radically and may cause discomfort for the user.

In existing solutions, the starting phase of the stimulus when the device is powered on is fixed and is not aligned with the user's inhalation phase. Users must adjust their inspiration or expiration phase to match the starting phase. Also, users must make adjustments to their breathing to keep in phase, and this can cause a user to need to interrupt their breathing to frequently synchronize their inspiration or expiration with the pacer. Users in other words may need to adjust their inhalation and exhalation phase according to the stimulation. As noted, this can cause an anxiety or stress response which disturbs the sleep induction state and therefore is contrary to the overall aim of sleep induction.

Thus, at least one set of embodiments of the present invention aim to address the problem that the phase of the stimulation may mismatch with the user's respiration phase.

FIG. 1 outlines in block diagram form components of an example processing device 32 according to one or more embodiments. The processing device 32 is adapted to execute steps of a method, and the method also forms an aspect of the invention. The features of the processing device will now be recited in summary, before being explained further in the form of example embodiments.

FIG. 1 shows the processing device 32 in the context of an exemplary arrangement in which it forms a component of a sleep aid apparatus 12. However, the processing device 32 can be provided as an aspect of the invention by itself. In some embodiments, it may be provided as a component of a sleep aid apparatus, as shown in FIG. 1. In some embodiments, it may be provided as part of a system comprising a sleep aid apparatus 12 and the processing device 32 separate from the sleep aid apparatus.

The processing device 32 comprises an input/output 34 and one or more processors 36.

The processing device is in general terms for use with a sleep aid apparatus 12 which comprises one or more stimulus generators 42 operable to generate one or more user-perceptible stimuli with one or more sensory modalities, and which comprises a physiological sensor 44 for sensing a physiological parameter of a user of the device. For example, the processing device may be arranged operatively coupled, for instance via the input/output 34, with the one or more stimulus generators 42 and the physiological sensor 44.

Figure 2:
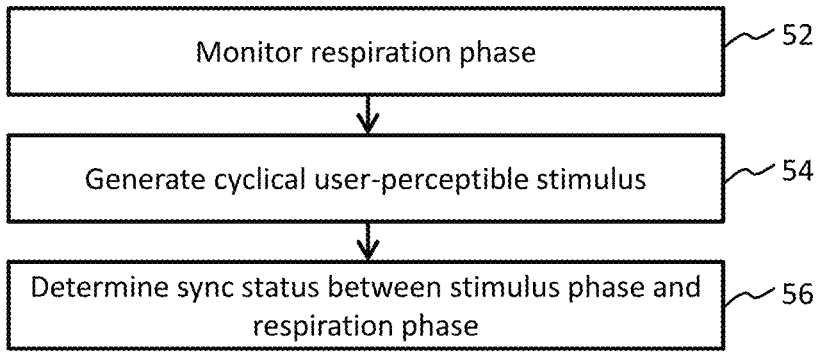
FIG. 2 outlines steps of an example method in accordance with one or more embodiments of the invention.

The processing device 36 is adapted to perform a method, for example using the one or more processing devices 36. The steps of the method in accordance with one or more embodiments are also shown in the form of a block diagram in FIG. 2.

The processing device 32 is adapted to monitor 52 a respiration phase of the user 46 based on processing of an input sensor signal from the physiological parameter sensor 44.

The processing device 32 is further adapted to control generation 54 of a first user-perceptible stimulus using at least a first stimulus generator 42 which is cyclically patterned for guiding a user in matching a pacing of their breathing to a cycle phase and cycle frequency of the first user-perceptible stimulus.

In some embodiments, the processing device is adapted to configure an initial cycle phase of the first user-perceptible stimulus based on the user respiration phase. For example, this ensures that the stimulus starts in phase-alignment with the user's breath.

In some embodiments, the processing device 32 is adapted to determine 56 a synchronization status between a cycle phase of the first user-perceptible stimulus and the user respiration phase. For example, this could be done at one or more points after the first user-perceptible stimulus has started, to check phase synchronization status. In some embodiments, the processing device 32 is further adapted to perform a response action based on the synchronization status.

In some embodiments, the processing device is adapted to: monitor the user's respiration phase over one or more cycles using the input physiological sensor signal; generate and start the cyclically patterned user-perceptible stimulus with its starting phase synchronized with the user's respiration phase at the moment of starting; optionally at one or more subsequent points during operation determine the synchronization status between the first user-perceptible stimulus phase and respiration phase; and optionally adjust the phase of the first user-perceptible stimulus for alignment with the user's respiration phase.

The physiological sensor mentioned above may be a heart rate sensor or pulse rate sensor. It may be a PPG sensor. The respiration cycle phase can be derived from a pulse or heart rate sensor signal. In particular, a signal can be derived of pulse rate as a function of time, and a start of an increase of the pulse rate signal can be taken to be aligned with the start of the inhalation phase, and the start of the decrease of the pulse rate signal can be taken to be aligned with the start of the decrease of the exhalation phase. Indeed, the rising part of a heart or pulse rate variation curve (heart or pulse rate as a function of time) corresponds to the inhalation phase, and the falling part of the signal corresponds to the exhalation phase. Thus, with the heart or pulse rate signal, the inhalation and exhalation phase could be easily detected. The breathing or respiration rate could also be detected through determining an interval frequency of the peaks of the heart rate signal.

With regards to the first user-perceptible stimulus, there are many different options for the sensory modality which is used. In one set of embodiments which will be described in greater detail to follow, a tactile stimulus is used for the first user-perceptible stimulus. With a tactile stimulation, users can close their eyes during the paced breathing activity, and their senses are minimally disturbed by the stimulus. One set of embodiments to be discussed later proposes to use an article which can be held against the body such as a hugging pillow which would expand and contract cyclically to communicate the guiding stimulus, and the user follows the pace of the expansion and contraction. This is an elegant solution since it mimics the organic motion of the chest cavity during breathing and so is an intuitively understandable stimulus for guiding breathing. For example, the article could undergo inflation and deflation of an internal air bag via control of a pump. Another example of tactile stimulation is use of a vibration motor, e.g. in a wrist band worn by the used or in a handheld device. A vibration device would consume less power and could have a size which is smaller than a pneumatic system for inflation/deflation. However, there are other ways to generate expansion and contraction of an article such as a pillow, such as more compact actuators.

It is noted that in the context of this disclosure, the reference to the 'phase' of the first user-perceptible stimulus cycle and the respiration cycle at a given time means the fraction of the cycle covered up to the given point in time. In other words, at a given point in time, the phase of either the stimulus cycle or the respiration cycle means the fraction of the current cycle which has been covered up to that given point in time. Typically, the phase might be represented mathematically by a single variable parameter, $\phi$, which ranges from a starting value of zero to a defined maximum value $\phi\_max$, (i.e. [0, $\phi\_max$]) and wherein, for a cycle having a Period (i.e. time duration) of T, the phase $\phi_1$ at time t might be given by $\phi_t=(\phi\_max/T)*t+\phi_{offset}$, where $\phi_{offset}$ is an offset or starting phase of the cyclical pattern.

As mentioned above, in some embodiments, the processing device 32 is further adapted to perform a response action based on the synchronization status. There are different options in respect of the response action. One general approach is to take steps to adjust the phase of the first user-perceptible stimulus to improve the synchronization status. Another general approach is to communicate a synchronization status to the user to assist the user in improving synchronization.

Figure 3:
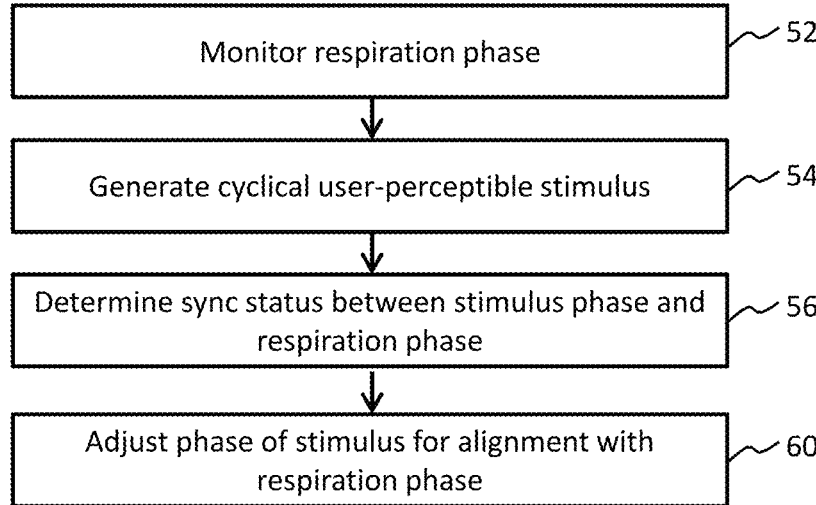
FIG. 3 outlines steps of a further example method in accordance with one or more embodiments of the invention.

Steps of an example method which is in accordance with the first general approach are outlined in block diagram form in FIG. 3. Further to the steps outlined in FIG. 2, this method comprises the additional step of performing 60 one or more adjustments of a current cycle phase of the first user-perceptible stimulus so as to align it (or at least to improve alignment, i.e. align it closer) with a current respiration phase of the user. In other words, a response action is performed which comprises the aforementioned one or more adjustments.

As mentioned above, preferably, the processing device may be adapted to configure an initial cycle phase of the first user-perceptible stimulus based on the user respiration phase. For example, this could be performed on start-up of the device, or upon starting the paced breathing guidance. This ensures that the stimulus starts in phase-alignment with the user's breath. For example, the processing device 32 may be adapted to execute a start-up routine comprising: monitoring a respiration phase for a plurality of respiration cycles of the user based on processing of an input sensor signal from the physiological sensor; starting the generating of the first user-perceptible stimulus; and wherein the first user-perceptible stimulus is started at a starting phase of its cyclical pattern, and wherein the starting phase is set to match a current cycle phase of the user's respiration cycle at the moment of the starting.

After starting, one or more adjustments may be made to the phase of the first-user-perceptible stimulus. In other words, one or more further adjustments may be made after the first user-perceptible stimulus has already started, based on monitoring of the user's breathing or respiration cycle throughout operation. The one or more adjustments could be performed at recurrent or repeating time points throughout an operating period. In some embodiments, the performing any one of the one or more adjustments may comprise, at a time point of performing the adjustment: detecting any disparity between the cycle phase of the first user perceptible stimulus and the respiration phase of the user; and adjusting the cycle phase of the first user-perceptible stimulus such that it matches (or better matches) the respiration phase of the user.

Figure 4:
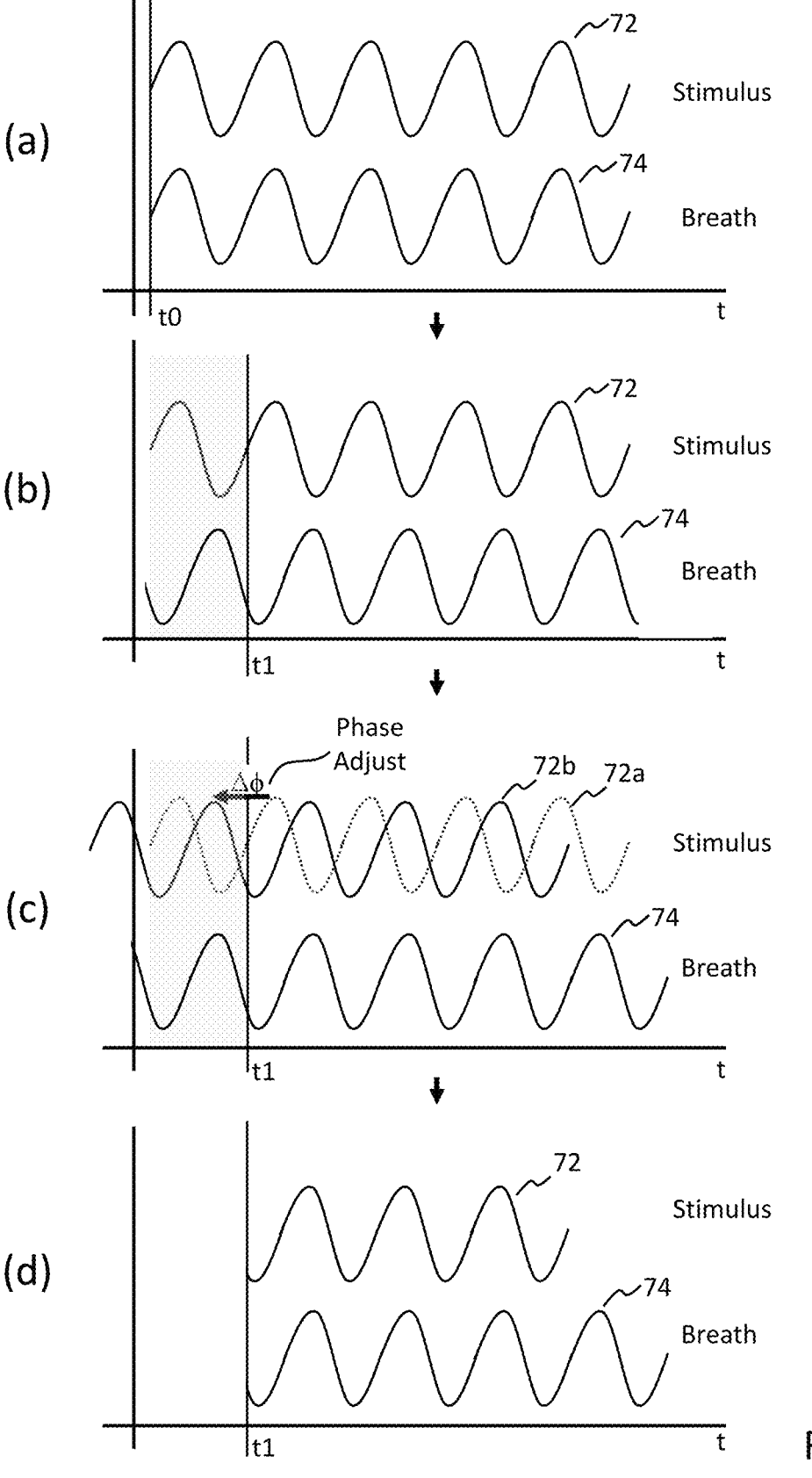
FIG. 4 schematically illustrates an example procedure for adjusting a cycle phase of a first user perceptible stimulus.

FIG. 4 schematically illustrates an example process of adjusting the phase, $\phi$, of an example first user-perceptible stimulus.

FIG. 4 (a) shows a waveform 72 of the example first user-perceptible stimulus. The waveform is indicative of the cyclical patterning of the first user-perceptible stimulus. For example, the waveform represents an intensity of the generated stimulus as a function of time, for thereby guiding the user in modulating their breathing in correspondence with the cyclically patterned stimulus. FIG. 4(a) further shows a waveform 74 of the user's breath as a function of time. FIG. 4(a) indicates an initial time point to, at which the stimulus and the user's breathing cycle are in phase.

FIG. 4(b) indicates a later point in time, t1, at which the stimulus 72 and user's breathing phase 74 have fallen out of sync with one another, and so are no longer in phase.

FIG. 4(c) schematically illustrates an example adjustment, $\Delta\phi$, of the phase of the first user-perceptible stimulus 72. In this example, the adjustment comprises translating the phase of the first user-perceptible stimulus by a phase difference or phase shift, $\Delta\phi$, so as to align it thereby align it with a current respiration phase of the user at the time t1. Waveform 72a indicates the first user perceptible stimulus waveform before the phase adjustment, and waveform 72b indicates the first user-perceptible stimulus waveform after the phase adjustment.

FIG. 4(d) shows the waveform 72 of the first user perceptible stimulus after the phase adjustment, at time t1. The first user-perceptible stimulus then proceeds in accordance with the same patterning and frequency as before, but with the phase aligned at time t1 with the phase of the breath cycle.

It is noted that preferably the particular cyclical pattern followed by the first user-perceptible stimulus, including for example the frequency or period of the stimulus, is set and controlled independently of any phase adjustments that may be performed. To state this more precisely, in some embodiments, the controlling generation of the first user-perceptible stimulus comprises controlling a cycle frequency or cycle period of the first user-perceptible stimulus, and wherein the one or more adjustments of the cycle phase of the first user-perceptible stimulus are performed independently of the control of the cycle frequency or cycle period of the stimulus. In other words, the one or more adjustments of the cycle phase of the user-perceptible stimulus are performed without changing an underlying period or frequency of the cyclically patterned first user perceptible stimulus. For example, during periods in-between said repeating time points, the first user-perceptible stimulus may be generated with a fixed or independently controlled cycle frequency.

It is noted that in the context of this disclosure, the terms cycle frequency and cycle period, applied in respect of the first user perceptible stimulus means the frequency of repetition of each cycle of the cyclical pattern embodied by the first user-perceptible stimulus. This might be a smooth, sinusoidal pattern, or could be a differently shaped pattern, for example being skewed for guiding a longer expiration than inspiration. For example, each cycle of the cyclically patterned first user-perceptible stimulus might include an inhalation phase portion, and an exhalation phase portion, and the durations of the inhalation and exhalation phase portions might be different to one another. In other words, a ratio between an inhalation and exhalation phase portion duration may not be 1:1. For example it could be 1:2. A longer exhalation cycle is helpful to modulate the parasympathetic nerve system, and is good for relaxation. For example, the ratio of inhaling duty to exhaling duty in one breathing cycle could be 1:1 or 1:1.5 or 1:2 etc. In all cases, the stimulus will exhibit a repeating 'unit' or 'cycle' of the pattern, and the frequency means the frequency of repetition of this unit or cycle, and the period means the time duration spanned by one instance of this unit or cycle of the pattern. The phase means the fraction of the particular cycle currently in progress which has been moved through at the given time point.

By way of illustration, an example implementation of the method according to a particular set of embodiments considered particularly advantageous by the inventors, could be summarized as comprising the following steps/features:

Start the inhalation phase of the first user-perceptible stimulus (i.e. the phase which is for guiding a user to inhale) responsive to detection using the physiological parameter sensor of a start of an inhalation of the user. This might be performed upon device switch-on for example. This corresponds to the start-up routine mentioned previously for example Extend or shorten a current user-perceptible stimulus cycle to make the stimulus match the phase of the user's inhalation/exhalation, for example responsive to detecting an asynchrony in phase.

Optionally, the method also comprises monitoring a stability of a user's breathing cycle, and the above one or more adjustments of the user-perceptible stimulus are only performed responsive to detecting that the user's breathing is relatively steady. This thereby filters out unexpected noise and makes the system overall more stable.

An overall aim may be to automatically adjust the first user-perceptible stimuli to match the inhalation or exhalation phase, but preferably to maintain the underlying guiding frequency of the first user-perceptible stimulus.

There will now be described optional features for configuring a frequency or period of the first user perceptible stimulus. These features may be embodied in a device or method according to one or more embodiments. The features described may be combined with any of the one or more embodiments already described above, or may be provided as a separate aspect of the invention.

In some embodiments, the processing device is adapted to control the cycle frequency of the first user-perceptible stimulus in dependence upon a physiological parameter determined from processing of the physiological sensor signal.

In some embodiments, to now be discussed in more detail below, the method further comprises processing the physiological sensor signal to determine a heart rate variability (HRV) of the user, and setting a frequency of the first user-perceptible stimulus in dependence thereon.

According to a particular aspect of the invention, there is provided a processing device for a sleep-aid apparatus, the sleep aid apparatus comprising one or more stimulus generators operable to generate one or more user-perceptible stimuli with one or more sensory modalities, and the sleep aid apparatus further comprising a physiological sensor.

The processing device is adapted to:
receive an input sensor signal from the physiological sensor;

control generation of a first user-perceptible stimulus which is cyclically patterned for guiding a user in matching a pacing of their breathing to a cycle phase and cycle frequency of the first user-perceptible stimulus; and wherein the processing device is adapted to control a cycle frequency of the first user-perceptible stimulus in dependence upon a physiological parameter determined from processing of the physiological sensor signal.

Figures 5, 6, 7:
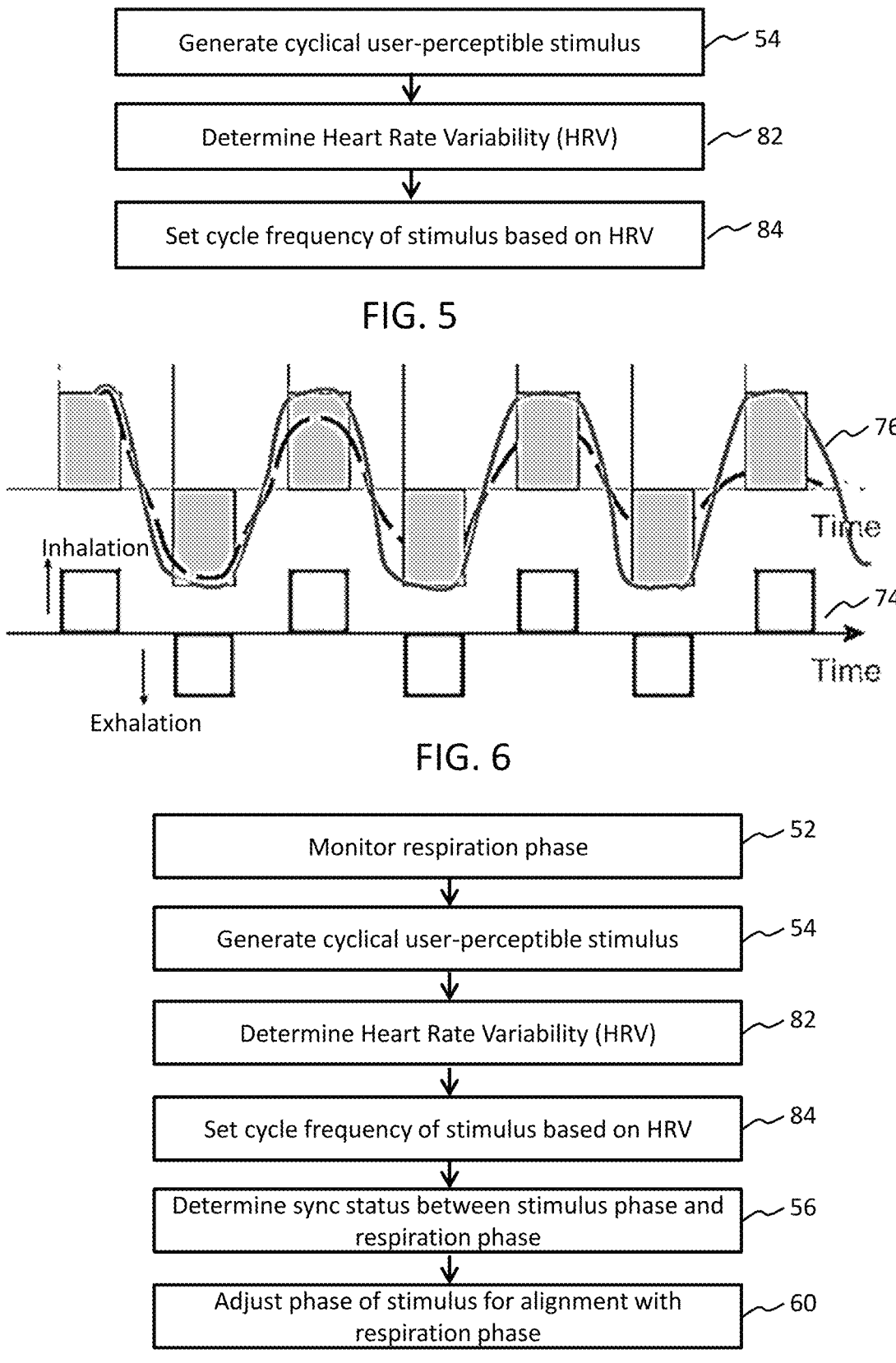
FIG. 5 outlines steps of a further example method in accordance with one or more embodiments of the invention.
FIG. 6 illustrates heart rate variability (HRV) relative to respiration phase.
FIG. 7 outlines steps of a further example method in accordance with one or more embodiments of the invention.

FIG. 5 outlines in block diagram form steps of an example method according to one or more embodiments. The steps will be recited in summary, before being explained further in the form of example embodiments. The method comprises: controlling generation 54 of a first user-perceptible stimulus which is cyclically patterned for guiding a user in matching a pacing of their breathing to a cycle phase and cycle frequency of the first user-perceptible stimulus; processing the physiological sensor signal to determine or monitor 82 a heart rate variability (HRV) of the user, and setting 84 a frequency of the first user-perceptible stimulus in dependence thereon.

It is noted that the order of steps could be different. For example, step 54 of generating the user-perceptible stimulus might be performed only after the cycle frequency has been set, so that the first-user perceptible stimulus starts with the HRV-adapted frequency. However, the cycle frequency could also be adjusted after the first user-perceptible stimulus has already started. For example, it could be started with a default cycle frequency, and adjusted after starting.

The steps of this method could be combined with those of any of the other methods described in this disclosure, e.g. as outlined in FIG. 7 (to be described later). In addition to this, the method of FIG. 5 represents an invention in its own right, since it provides by itself the advantageous technical effect of improving efficacy of the paced breathing guidance by tailoring the frequency of the guiding stimulus according to the user's HRV. Thus, this method may be provided as a separate aspect of the invention. Also, a processing device configured to perform the method is an aspect of the invention. Also, a computer program product comprising instructions which, when executed on a processing device, to cause the processing device to perform the method is another aspect of the invention.

As will now be explained in further detail, HRV is an important biological indicator for determining best parameters of paced breathing.

Heart rate is not constant, but varies from beat to beat. In particular, the heart rate increases with the start of inhalation and drops when an individual starts to exhale. This is illustrated schematically in FIG. 6 in which line 76 indicates an example heart rate of an individual, and this is shown superimposed over inhalation and exhalation phases 74 of the user. This illustrates the concept that heart rate increases with inhalation, and decreases with exhalation.

Furthermore, the degree of heart rate irregularity varies depending upon arousal state. When an individual is in a stress state, their heart beats more regularly and, when an individual is in a more relaxed state, their heart beats more irregularly. This can be expressed by the parameter of Heart Rate Variability (HRV). Low HRV corresponds to a more stressful state. Indeed, persistently low HRV can even be a cause of death. Higher HRV corresponds to a more relaxed state.

Furthermore, a person's breathing pace affects their level of relaxation, via the biofeedback of the cardiovascular system.

In the context of sleep induction, an aim would be to achieve the maximally relaxed state (state of minimal arousal, or minimal stress). This would correspond to a state of highest HRV. It is known that breathing pace can change a person's degree of stress versus relaxation. Thus, an aim would be to set the frequency or period of the cyclically patterned first user-perceptible stimulus so that it guides the user to adopt a (matching) breathing pace which induces the highest possible HRV for that user. In other words, the aim is to guide the user to adopt that breathing pace which is correlated with the highest HRV achievable for that user. Within the technical field, the term 'resonant HRV frequency' is sometimes used to denote this breathing cycle frequency correlated with highest HRV.

By way of a rough guide, this resonant frequency is typically in the range of 4.5-6.5 breaths per minute, and varies between different individuals, and even varies for a same individual at different times, according to his/her physiological status.

In some embodiments, the processing device may be configured to set the cycle frequency of the first user-perceptible stimulus equal to a frequency correlated with a highest HRV of the user.

There may be included a procedure for determining the breathing frequency of the user which is correlated with a highest HRV.

This procedure may involve varying the cycle frequency of the first user-perceptible stimulus, measuring the HRV at each cycle frequency, and then setting the cycle frequency of the first user-perceptible stimulus equal to the cycle frequency among the different set frequencies which coincided with a highest measured HRV amplitude.

By way of example, there may be implemented a calibration procedure for setting the cycle frequency of the first user-perceptible stimulus, the calibration procedure comprising a series of epochs, and wherein: the cycle frequency of the first user-perceptible stimulus is set at different respective values in each respective epoch; during each epoch, the physiological sensor signal is processed to determine an HRV of the user; the cycle frequency of the first user-perceptible stimulus is set equal to the cycle frequency during the calibration procedure which coincided with a highest measured HRV.

By way of example, the different respective values of the cycle frequency in the different epochs could be set at frequencies which vary across a window which spans a pre-defined typical range of a HRV resonant frequency values for individuals. For example, this could be a window centered on e.g. 5.5 breaths per minute.

The physiological sensor mentioned above may be a heart rate sensor or pulse rate sensor. It may be a PPG sensor. HRV can be derived through a pulse or heart rate signal.

Furthermore, the respiration cycle phase can also be derived from a pulse or heart rate sensor. In particular, a start of an increase of the pulse rate is aligned with the start of the inhalation phase, and the start of the decrease of the pulse rate is aligned with the start of the decrease of the exhalation phase. Indeed, the rising part of a heart or pulse rate variation curve (heart or pulse rate as a function of time) corresponds to the inhalation phase, and the falling part of the signal corresponds to the exhalation phase. Thus, with the heart or pulse rate signal, the inhalation and exhalation phase could be easily detected. The breathing rate could also be detected through determining an interval frequency of the peaks of the heart rate signal.

Compared with ECG-based HRV detection, the precision of the HRV measurement may be lower. However, in the context of the present invention, the absolute values of the HRV are not essential; rather it is only the identification of the maximum HRV measurement relative to other HRV measurements that is needed, so that the correlated stimulus frequency associated with this maximum HRV can be identified. As explained above, the frequency of the first user-perceptible stimulus which is correlated with the highest HRV amplitude corresponds to the HRV resonant frequency.

Thus, the pulse sensor can be used to determine the HRV resonant frequency of the user, and this can be used to set the frequency of the first user perceptible stimulus, to guide the user to a breathing pace which is known to correlate for that user with a maximum HRV. In other words, the HRV resonant frequency is used as the target guidance breathing frequency for the sleep induction. In this way, a personalized paced breathing stimulation device can be achieved.

The steps associated with setting the cycle frequency of the first user-perceptible stimulus could be combined with the steps of any of the other methods described in this disclosure or provided by themselves. By way of example, FIG. 7 outlines in block diagram form steps of an example method according to one or more embodiments. The details of each of the steps have already been described in this document, and thus the reader is referred to relevant passages above for further details. The method comprises; monitoring 52 a respiration phase of the user based on processing of an input sensor signal from the physiological sensor; controlling generation 54 of a first user-perceptible stimulus which is cyclically patterned for guiding a user in matching a pacing of their breathing to a cycle phase and cycle frequency of the first user-perceptible stimulus; processing the physiological sensor signal to determine 82 or monitor a heart rate variability (HRV) of the user, and setting 84 a frequency of the first user-perceptible stimulus in dependence thereon; and determining 56 a synchronization status between the cycle phase of the first user-perceptible stimulus and the user respiration phase. The method may further comprise performing a response action such as performing 60 one or more adjustments of the cycle phase of the first user-perceptible stimulus so as to align it with a current respiration phase of the user. Step 82 and step 84 could instead be performed in advance of starting the generation of the first user-perceptible stimulus, so that the stimulus starts with a cycle frequency determined based on the HRV.

An example implementation of the method according to a particular set of embodiments will now be described by way of further illustration. It will be appreciated that not all features of this particular set of embodiments are essential to the inventive concept, and are described to aid understanding and to provide an example to illustrate the inventive concepts.

In a first step, a user puts their finger on a pulse sensor integrated in the sleep aid apparatus. For example, the sleep aid apparatus may comprise an article adapted for being in contact with a user during use, for example a cushion or pillow, and the pulse sensor is integrated in the article and designed so as to have a sensitive area accessible to physical contact at a surface of the article. The user breathes at this stage according to their own pace.

The inhalation and exhalation phase of the user is detected through the pulse signal, and a start of the cyclically patterned first user-perceptible stimulation is started at such a time so as to be synchronized in phase with the inhalation phase or exhalation phase of the user. For example, in some embodiments (to be described in greater detail to follow), the first user-perceptible stimulus is a tactile or haptic stimulus and comprises a cyclical motion induced by an actuation mechanism. For example, in some embodiments, the cyclical motion comprises cyclical expansion and contraction of at least a part of an article adapted for being in contact with a user during use. For example, the actuation mechanism may be a pneumatic actuation mechanism, and wherein the first user-perceptible stimulus comprises cyclical inflation and deflation of a bladder integrated inside said article. In this case, the article might be controlled so as to start inflating when the user starts inhalation, and start deflating when the user starts to exhale.

Thus, the start phase of the first user-perceptible stimulus is synchronized automatically with the user's breathing phase. During the stimulation, the synchronization could be adjusted to correct any asynchrony which has developed, e.g. through a short pause of the stimulation. This concept has already been described in some detail previously.

The stimulation frequency may then be set to the HRV resonant frequency (see discussion above for more details). By way of brief reminder, the HRV resonant frequency could be obtained in one of the following ways. By of one example, there may be implemented a calibration or practice phase to detect the HRV resonant frequency. For example, the user triggers the calibration phase, and during this phase they perform a practice use. In this calibration phase, the frequency of the first user-perceptible stimulus would be set at a series of different values, e.g. around 4.5, 5, 5.5, 6, 6.5 cycles per minute, e.g. for 2 minutes each. The corresponding HRV amplitude can be detected for each, through the pulse signal as described previously The HRV resonant frequency is the frequency value of the first user-perceptible stimulus which coincides with the maximum measured HRV amplitude during the calibration phase. This HRV resonant frequency is stored and used as the cycle frequency of the first user-perceptible stimulus during the main phase of operation of the device for sleep induction.

As an alternative to the above, the resonant HRV amplitude can be derived during the main phase of operation for sleep induction. In particular, during main operation, the frequency of the first user perceptible stimulus could be varied across a series of different values, e.g. starting at 5.5 cycles per minute, decreasing by 0.5 cycles per minute to 5 cycles per minute after 2 minutes and increasing to 6 cycles per minute after a further 2 minutes. The stimulation frequency which leads to the highest measured HRV frequency over this procedure is recorded as the HRV resonant frequency and is stored for use. The cycle frequency of the first user-perceptible frequency is then set as the determined HRV resonant frequency until sleep onset occurs.

The processing device may include a memory for storing the determined value of the HRV resonant amplitude.

In some embodiments, first contact of the user's body with the pulse sensor may be detected, and wherein a respiration phase of the user is monitored automatically responsive to this detection, and a start of the first user-perceptible stimulus is triggered so as to start in-phase with the user respiration cycle.

During the main sleep induction operation, the user controls their breath so as to follow the paced stimulation. After sleep onset, a user's breath frequency will typically start to increase, e.g. from around 5.5 breaths per minute during sleep induction to around 15 breaths per minute after sleep onset. At same time the heart rate will decrease compared to during an awake state. These two conditions, i.e. breathing rate increase and heart rate decrease, could be used together to detect the sleep onset. Responsive to sleep onset being detected, the processing device may be adapted to cease the first user-perceptible stimulus to avoid disturbing the sleep of the user.

In some embodiments, the frequency of the first user-perceptible stimulus could be adjusted gradually during sleep induction in a phase-synchronized way. For example, the breathing frequency of an adult may typically have a value of around 12-18 cycles per minute, while the HRV resonant frequency may typically be at a value of around 5.5 cycles per minute. In order not to suddenly jump to a much lower frequency (which might be uncomfortable), a transition phase might be implemented in which the cycle frequency of the user-perceptible stimulus is adjusted downward in stepwise fashion from a starting value (e.g. a pre-defined value, or a value which matches the user's current respiration frequency) to a value which matches the determined target cycle frequency, computed from the HRV. For example, when the first user-perceptible stimulus starts, it may be controlled to start at a frequency of 70% of the user's breathing rate (e.g. 12*0.79 bpm) for 2 minutes and then switch down a further 70% again if the frequency is still higher than HRV resonant frequency and so on until the determined target cycle frequency is reached. The step size, e.g. the percentage drop, could be varied, e.g. 60%, 75%, or 80% etc. It could be varied between steps in some examples, for example getting smaller as the target cycle frequency is approached. This step size could be manually adjusted or automatically adjusted.

As previously discussed, in some embodiments, in addition to or instead of adjusting a phase of the first user-perceptible stimulus, the processing device 32 may be adapted to control generation of a second user-perceptible stimulus indicative of the synchronization status between the cycle phase of the first user-perceptible stimulus and the user breathing phase. In some embodiments, the sleep aid apparatus may further comprise a second stimulus generator for generating the second user-perceptible stimulus.

Figure 8:
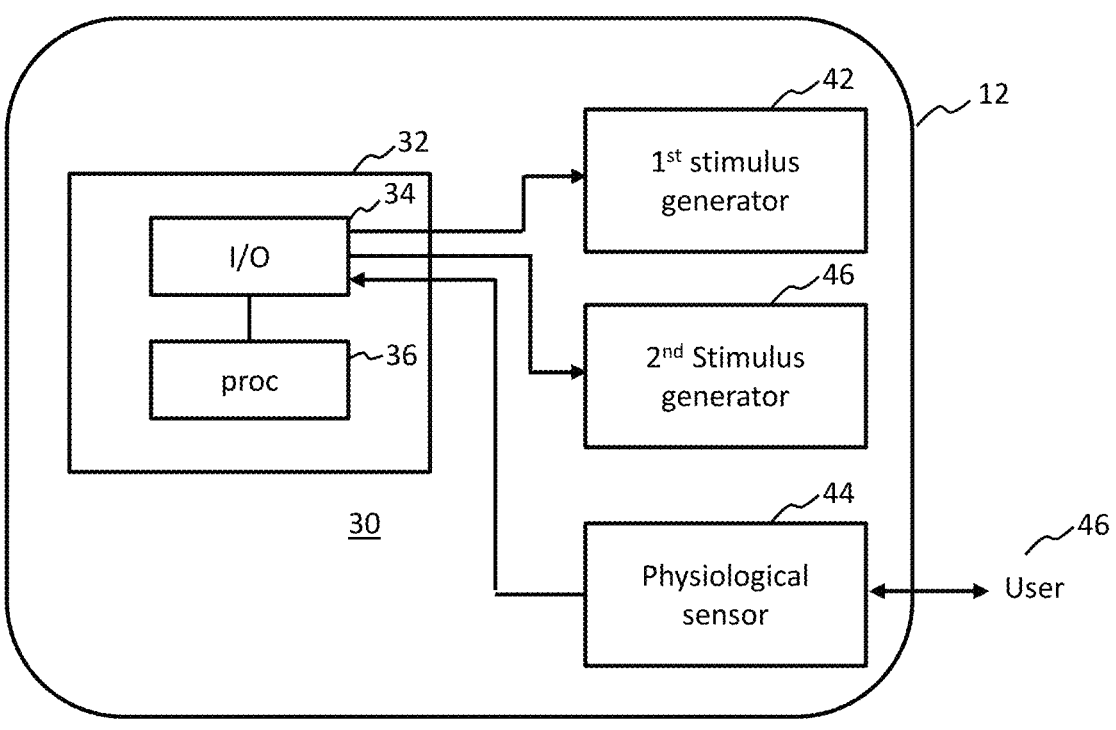
FIG. 8 schematically illustrates components of a further example sleep aid apparatus comprising a processing device in accordance with one or more embodiments of the present invention.

FIG. 8 schematically outlines components of an example sleep aid apparatus 12 in accordance with one or more embodiments of the invention. This sleep aid apparatus may be the same as the apparatus of FIG. 1 in all respects except for the additional inclusion of a second stimulus generator 46. This represents an example only. In some embodiments (and as will be described further later), the second user-perceptible stimulus may be generated by the same stimulus generator as the first user perceptible stimulus.

In one advantageous implementation, the first user-perceptible stimulus might comprise a cyclical expansion and contraction of at least a part of an article adapted for being in contact with a user during use, and wherein the second user-perceptible stimulus comprises a vibration. The two stimuli might be generated simultaneously with one another.

Figure 9:
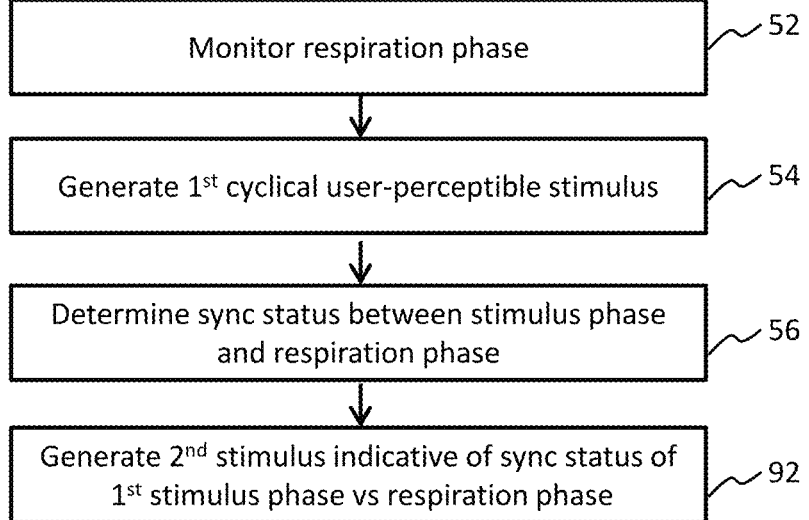
FIG. 9 outlines steps of a further example method in accordance with one or more embodiments of the invention.

FIG. 9 outlines steps of an example method in accordance with one or more embodiments of the invention. For example, the processing device 32 of FIG. 8 might be adapted to execute this method. This method can be provided as a separate aspect of the invention, the processing device 32 of FIG. 8 configured to execute this method could be provided as a separate aspect of the invention; and/or the sleep aid apparatus 12 of FIG. 8 comprising the processing device 32 could be provided as a separate aspect of the invention. In summary, the method comprises the steps of: monitoring 52 a respiration phase of the user based on processing of an input sensor signal from the physiological sensor 44; controlling 54 generation of a first user-perceptible stimulus which is cyclically patterned for guiding a user in matching a pacing of their breathing to a cycle phase and cycle frequency of the first user-perceptible stimulus; determining 56 a synchronization status between the cycle phase of the first user-perceptible stimulus and the user respiration phase; and controlling generation 92 of a second user-perceptible stimulus indicative of the synchronization status between the cycle phase of the first user-perceptible stimulus and the user breathing phase.

An example implementation of the method according to a particular set of embodiments will now be described by way of illustration of the above-summarized concept. It will be appreciated that not all features of this particular set of embodiments are essential to the inventive concept, and are described to aid understanding and to provide an example to illustrate the inventive concepts.

Normal breathing of an individual is cyclical, analogous to a tidal cycle, with the repetition of inhalation and exhalation phases.

Figure 10:
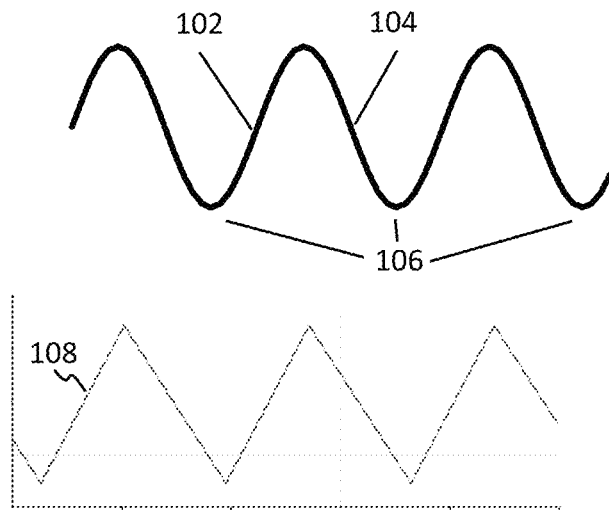
FIG. 10 illustrates one approach to patterning a second user-perceptible stimulus in accordance with one or more embodiments.

FIG. 10 (top) illustrates this respiration cycle change. During the inhalation phase 102, the chest wall is contracted and, during the exhalation phase 104, the chest wall is relaxed. After each exhalation phase 104, there is a natural pause 106 in respiration before the next inhalation 102 starts. During breathing, individuals feel a pressure change periodically in a manner analogous to tidal cycles.

In some embodiments, to simulate this tidal change of pressure, the first user perceptible stimulus 54 may be controlled progressively in a cyclical manner. This is achieved in practice by a first user-perceptible stimulus in the form of a vibration stimulus, and wherein an amplitude of the vibration is cyclically or periodically patterned to provide the cyclical patterning of the stimulus for guiding the user in their breathing pace.

FIG. 10 (bottom) shows a waveform 108 schematically illustrating an example of the cyclical patterning of the first user-perceptible stimulus according to one or more embodiments. It is shown in phase-alignment with the respiration cycles (top) of the user. The waveform 108 indicates a vibration amplitude change as a function of time.

The amplitude change illustrated in FIG. 10 follows a linear ramp-up during the inhalation phase, and linear ramp-down during the exhalation phase. However, non-linear variation of the vibration amplitude could also be performed. With this approach, the feeling of the vibration increases during the inhalation cycle and decreases during the exhalation cycle. Through this progressive change of the vibration amplitude, users could easily follow the pace of the guiding stimulation with their eyes closed and without disturbance to a peaceful state of mind.

It is noted that the above-described approach to generating the first user-perceptible stimulus could in fact be implemented as part of any of the embodiments described in this disclosure.

Continuing with the description of the present example set of embodiments, the method further includes monitoring a respiration phase 52 of the user while the first user-perceptible stimulus is being generated. This can be achieved using for example a heart or pulse rate signal in a manner already discussed above. For example, a PPG sensor is one simple way to obtain such a signal.

With the detection of the respiration or breathing rate of the user, a synchronization status of the user's breathing with the first user-perceptible stimulus could be determined 56 and fed back 92 to the user through a second user-perceptible stimulus. As discussed previously, it could arise that, while the user is following the correct breathing frequency or pace, that nonetheless the phase of their breathing cycle is out of sync with that of the guiding first user-perceptible stimulus, or even totally inversed. For example, the stimulation is in the inhalation phase, but the user is in exhalation phase.

There are different options for the feedback to the user of the synchronization status, to be discussed below: it may be generated with a different sensory modality to the first stimulus; it may be generated with the same sensory modality as the first, e.g. as a modulation of the first stimulus. In some examples, the feedback of the synchronization status may be haptic feedback, e.g. either with fixed strength or progressive vibration strength.

According to one example implementation, the previously discussed cyclically varying vibration stimulation could be used as a second user-perceptible stimulus (e.g. in addition to a separate first user-perceptible stimulus which guides the user in their breathing pace), and wherein this second stimulus is: continuously generated when the user's breathing phase is synchronized with the cycle phase of the first user-perceptible stimulus; and not generated when the user's breathing phase is non-synchronized with the cycle phase of the first user-perceptible stimulus. For example, the second user-perceptible stimulus comprises a vibration stimulus, and when the user's breathing phase is synchronized with the cycle phase of the first user-perceptible stimulus, an amplitude of the vibration is modulated in synchrony with the user's breathing phase.

For example, this implementation could be understood from the following example cases:

Case 1: the first user-perceptible stimulus is in the inhalation phase and the user's respiration is in the inhalation phase. In this case, the second user-perceptible stimulus is generated as a continuous vibration which is increased in amplitude (i.e. intensity) progressively in sync with the user's respiration phase.

Case 2: the first user-perceptible stimulus is in the inhalation phase and user's respiration is in the exhalation phase. In this case, the second user-perceptible stimulus is ceased, i.e. no vibration is fed back to the user, or a different pattern of vibration is used for the second user-perceptible stimulus, e.g. a series of short vibrations could be fed back to communicate to the user that there is a phase mismatch.

Case 3: the first user-perceptible stimulus is in the exhalation phase and the user's respiration is in the exhalation phase. In this case, the second user-perceptible stimulus is generated as a continuous vibration whose amplitude (i.e. intensity) is decreased progressively in sync with the user's respiration phase.

Case 4: the first user-perceptible stimulus is in the exhalation phase and the user's respiration is in the inhalation phase. In this case, the second user-perceptible stimulus is ceased, i.e. no vibration is fed back to the user, or a different pattern of vibration is used for the second user-perceptible stimulus, e.g. a series of short vibrations could be fed back to communicate to the user that there is a phase mismatch.

As a more general principle, in accordance with this exemplary approach, the feedback and feedback strength provided by the second user-perceptible stimulus allow the user to feel his or her breathing through positive feedback vibration during those times when their breathing is synchronized with the first user-perceptible stimulus (which guides their paced breathing).

Within the above example implementation, the first user-perceptible stimulus could be another vibration stimulus, or could be a stimulus of a different modality. For the case that vibration is to be used as the first user-perceptible stimulus, an additional vibrator could be used to provide the synchronization status feedback. Alternatively, both the first and second stimuli could be generated with a single vibrator, and wherein the second user-perceptible stimulus comprises a modulation of a baseline or offset of the cyclical pattern of the first user-perceptible stimulus. In other words, the baseline vibration strength of the first stimulus (for guiding the breath pace) could be increased, e.g. by 20%, when the stimulus phase is synchronized with the user's respiration phase, and this baseline change could provide the second stimulus to communicate the synchronization status.

However, it is also noted that the above implementation for the second stimulus is not limited to use with a first user-perceptible stimulus which is vibratory. By way of example, the first user perceptible stimulus could be an optical or visual stimulus, or an acoustic stimulus, or a tactile stimulus such as the expanding/contracting article mentioned briefly above (and to be described further below).

For example, where the first user-perceptible stimulus is generated as an expansion/contraction of a hugging pillow, when the user's inhalation is synchronized with the pillow expansion, a continuous vibration response could be generated through the vibrator (as the second user-perceptible stimulus). When the user's inhalation is not synchronized with the expansion phase of the pillow, no vibration is fed back to the user, or a different pattern of vibration is generated to communicate the mismatch.

Thus, following the principles of the particular example implementation described above, components of one particularly advantageous set of embodiments might include the following:

A sleep aid device (e.g. wrist band, handheld device, or a hugging device) with stimulus means for generating paced stimulation for guiding a user in pacing their breathing, e.g. with progressive vibration to mimic the tide of inhalation and exhalation.

A sensor provided on the sleep aid device, e.g. a PPG senor, for use in tracking the inhalation and exhalation of the user.

A haptic feedback means (e.g. a like vibrator) to provide continuous feedback when the user's breathing is synchronized with the pace of the stimulation.

Figure 11:
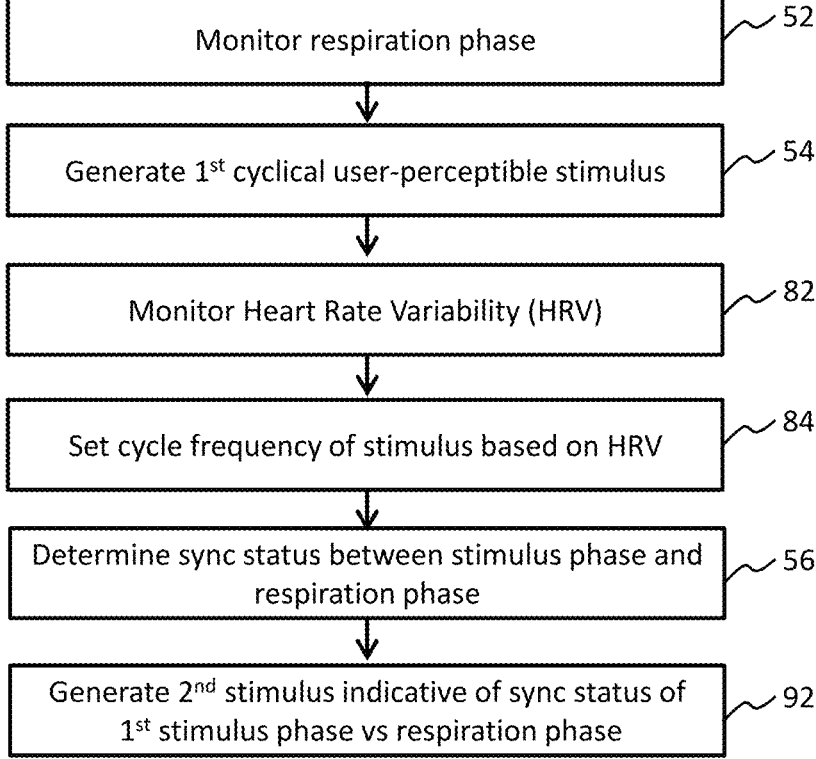
FIG. 11 outlines steps of a further example method in accordance with one or more embodiments of the invention.

Any of the features or method steps described above could be combined with, or integrated into, any of the other methods described in this document. By way of example, FIG. 11 outlines in block diagram form steps of an example method according to one or more embodiments. The details of each of the steps have already been described in this document, and thus the reader is referred to relevant passages above for further details. The method comprises: monitoring 52 a respiration phase of the user based on processing of an input sensor signal from the physiological sensor; controlling generation 54 of a first user-perceptible stimulus which is cyclically patterned for guiding a user in matching a pacing of their breathing to a cycle phase and cycle frequency of the first user-perceptible stimulus; processing the physiological sensor signal to determine or monitor 82 a heart rate variability (HRV) of the user, and setting 84 a frequency of the first user-perceptible stimulus in dependence thereon; determining 56 a synchronization status between the cycle phase of the first user-perceptible stimulus and the user respiration phase; and the controlling generation 92 of a second user-perceptible stimulus indicative of the synchronization status between the cycle phase of the first user-perceptible stimulus and the user breathing phase.

Optionally, step 82 and step 84 could instead be performed in advance of starting the generation 54 of the first user-perceptible stimulus, so that the stimulus starts with a cycle frequency determined based on the HRV.

Figure 12:
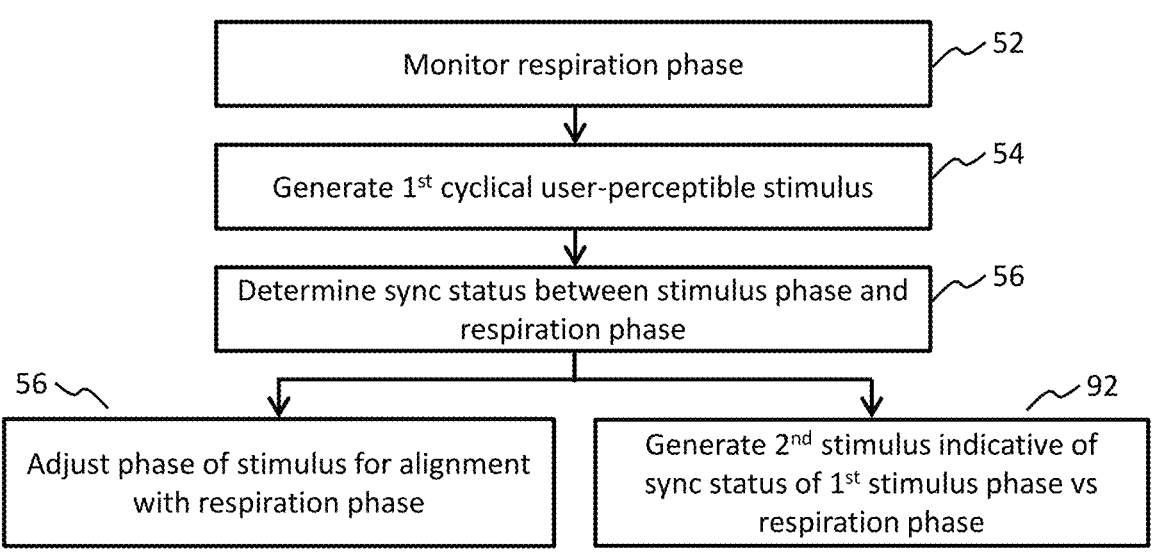
FIG. 12 outlines steps of a further example method in accordance with one or more embodiments of the invention.

By way of another example, FIG. 12 outlines in block diagram form steps of another example method according to one or more embodiments. The details of each of the steps have already been described in this document, and thus the reader is referred to relevant passages above for further details. The method comprises: monitoring 52 a respiration phase of the user based on processing of an input sensor signal from the physiological sensor; controlling generation 54 of a first user-perceptible stimulus which is cyclically patterned for guiding a user in matching a pacing of their breathing to a cycle phase and cycle frequency of the first user-perceptible stimulus; determining 56 a synchronization status between the cycle phase of the first user-perceptible stimulus and the user respiration phase. Based on the determined synchronization status, the method comprises performing two response actions: performing one or more adjustments 56 of the cycle phase of the first user-perceptible stimulus so as to align it with a current respiration phase of the user; and controlling generation 92 of a second user-perceptible stimulus indicative of the synchronization status between the cycle phase of the first user-perceptible stimulus and the user breathing phase.

Figure 13:
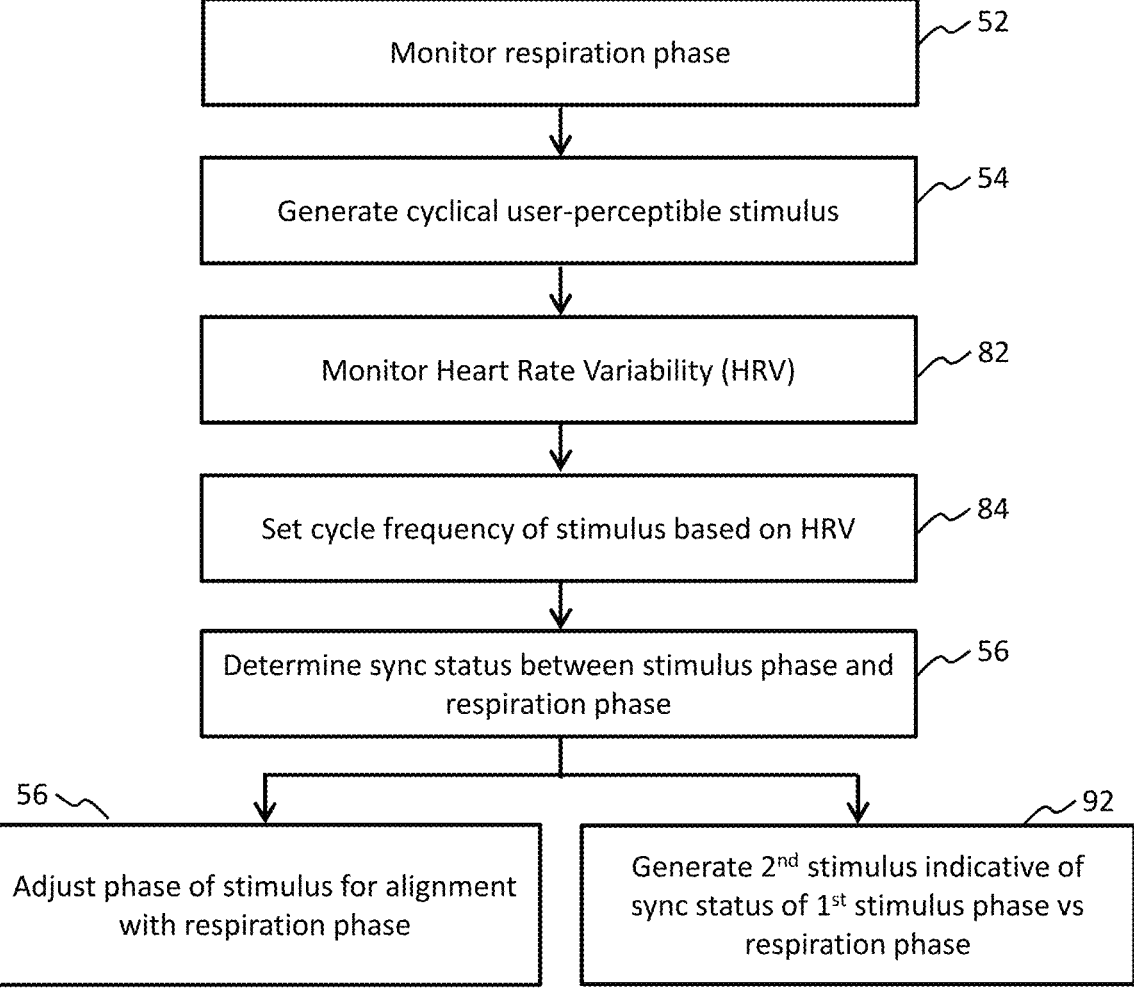
FIG. 13 outlines steps of a further example method in accordance with one or more embodiments of the invention.

By way of another example, FIG. 13 outlines in block diagram form steps of another example method according to one or more embodiments. This simply represents a combination of the methods of FIG. 11 and FIG. 12. The details of each of the steps have already been described in this document, and thus the reader is referred to relevant passages above for further details. The method comprises: monitoring 52 a respiration phase of the user based on processing of an input sensor signal from the physiological sensor; controlling generation 54 of a first user-perceptible stimulus which is cyclically patterned for guiding a user in matching a pacing of their breathing to a cycle phase and cycle frequency of the first user-perceptible stimulus; processing the physiological sensor signal to determine or monitor 82 a heart rate variability (HRV) of the user, and setting 84 a frequency of the first user-perceptible stimulus in dependence thereon; determining 56 a synchronization status between the cycle phase of the first user-perceptible stimulus and the user respiration phase. Based on the determined synchronization status, the method comprises performing two response actions: performing one or more adjustments 56 of the cycle phase of the first user-perceptible stimulus so as to align it with a current respiration phase of the user; and controlling generation 92 of a second user-perceptible stimulus indicative of the synchronization status between the cycle phase of the first user-perceptible stimulus and the user breathing phase.

It is noted that, in any of the above-described methods, the step of determining the cycle frequency of the first user-perceptible stimulus may be performed before the first user-perceptible stimulus is first generated, or after the first user-perceptible stimulus is first generated. Thus the particular ordering of steps indicated in each of the Figures is not essential, and the order of the steps could vary. For example, the method could comprise: initially monitoring the physiological sensor signal before starting the first user-perceptible stimulus; determining the HRV of the user; monitoring the respiration phase of the user; determining the cycle frequency to use for the stimulus, based on the HRV, using methods already described above; and starting the first user-perceptible stimulus with the determined cycle frequency, and preferably also at a starting phase which matches the respiration phase of the user at the point of starting.

Further optional details relating to the means for generating the first user-perceptible stimulus, and options related to the structure of the sleep aid apparatus, and compatible with any embodiment of the invention, will now be briefly described. Furthermore, the advantageous arrangement discussed below represents an invention of its own, since it provides advantageous technical effects which could be achieved independent of other features already discussed.

In accordance with one or more embodiments, it proposed to generate the previously discussed first user-perceptible stimulus (for guiding the paced breathing of the user) using an article which can be held by the user and which expresses a cyclical motion induced by an actuation mechanism, said cyclical motion providing the first stimulus. In some embodiments, it is proposed that at least a portion of the article undergo a cyclical expansion and contraction as the first user-perceptible stimulus.

Figures 14, 15, 16, 17:
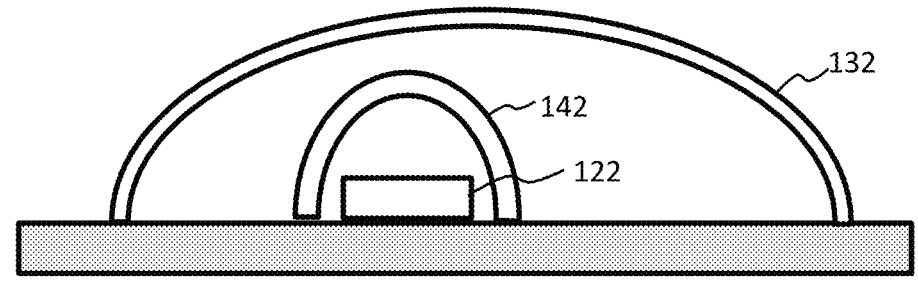
FIG. 14 illustrates an example sleep aid apparatus in the form of an article for holding against the body.
FIGS. 15-16 illustrate an example sleep aid apparatus according to one or more embodiments of the invention comprising an integrated physiological parameter sensor.
FIG. 17 illustrates features of the apparatus of FIGS. 15-16 for guiding finger placement over an example physiological parameter sensor.

FIG. 14 illustrates an example article 112 in the form of a cushion or pillow. The cushion or pillow could be for being held by the user against the body. This might be referred to as a hugging pillow. For example, it might be contoured or shaped so as to conform with the shape of the body, for comfortably holding against the body. The expansion and contraction of the device would be felt by the user and guide the user to follow the motion pacing with their breath.

By way of example, the actuation mechanism may be a pneumatic actuation mechanism, and wherein the first user-perceptible stimulus comprises cyclical inflation and deflation of a bladder integrated inside said article 112. For example, a hugging pillow might be provided which is designed to inflate to prompt the user to inhale and deflate to prompt the user to exhale.

According to one or more embodiments, there may be provided a system comprising a processing device in accordance with any of the embodiments already discussed (for example in accordance with the embodiment of FIG. 1 or FIG. 8), and further comprising the article as described above for providing the first stimulus generator.

According to one or more embodiments, there may be provided a sleep-aid apparatus comprising: one or more stimulus generators operable to generate one or more user-perceptible stimuli with one or more sensory modalities; a physiological sensor; and the processing arrangement in accordance with any embodiment described in this document.

A preferred implementation of a sleep aid apparatus according to a particular set of embodiments will now be described by way of illustration. It will be appreciated that not all features of this particular set of embodiments are essential to the inventive concept, and are described to aid understanding and to provide an example to illustrate the inventive concepts.

In this set of embodiments, it is proposed to provide a sleep aid apparatus which comprises an article for making physical contact with a user during sleep induction, and wherein the physiological sensor is integrated in the article. For example, the article could be a pillow or cushion, such as the hugging pillow already mentioned above. However, more generally, the article could be any item which can be held by the user. The article may preferably have a textile surface and/or be cushioned at least at its surface. The article is preferably suitable for holding by a user against their body with one or more hands, i.e. for grasping or hugging by a user, thereby bringing their hand into continuous contact with the device.

With regards to the physiological sensor, it is proposed preferably to use a PPG sensor arranged so as to have a sensitive area accessible to physical contact at a surface of the article. This allows a user's heart rate to be monitored continuously while they hold the article, while the expansion and contraction (or other stimulus) provides the guidance for the user in pacing their breathing.

The heart rate can be used to track the respiration phase of the user. Furthermore, and as has already been discussed above, the heart rate can be used in some embodiments to determine the HRV biofeedback resonant frequency (meaning the frequency of paced breathing which stimulates the user to manifest a highest HRV). The resonant frequency can optionally be used as the target guidance breathing frequency for the sleep induction.

As discussed above, in some embodiments, the phase of first user-perceptible stimulus which provides the respiration guidance can be automatically adjusted to align with the inhalation/exhalation phase of the user through the use of the PPG signal to track the respiration phase. This assists the user to breath synchronously with the pace of the respiration guidance.

Optionally, the start and stop of the first user-perceptible stimulus could be triggered automatically according to the sleep/wake status of the user.

Advantageous features according to a particular one or more embodiments are illustrated schematically in FIG. 15, FIG. 16 and FIG. 17.

As shown in FIG. 15, it is proposed to provide the article 112 with an integrated physiological parameter sensor 122 arranged with a sensitive area accessible to physical contact at a surface of the article. For example, it is proposed to mount a pulse sensor on the surface of the article.

Furthermore, as illustrated in FIG. 16, it is proposed in some embodiments to provide a pocket or cover element 132 extending over the sensitive area of the sensor 122 which permits the user to put in his or her hand 124. For example, the pocket or cover element 132 is attached to a surface of the article, and wherein the sensitive area of the sensor 122 is accessible to physical contact via an opening of the pocket or cover element.

As illustrated in FIG. 16 and FIG. 17, in some embodiments, the apparatus further includes a finger placement guide 142 for guiding a user in physical placement of their finger over the sensitive area of the sensor 122. This assists in fixing the position of user's finger relative to the sensor 122, to obtain a stable pulse signal detection. In the illustrated example, this finger placement guide 142 comprises a band, or a ring-like belt, extending over the pulse sensor, and through which a user can insert their finger for holding the finger in place. More generally, a finger placement guide might be provided which is able to provide physical or tactile guidance, for guiding placement of the finger without visual observation by the user. The finger placement guide is preferably adapted to releasably hold the finger in place.

In some embodiments, integrated within an internal space of the article 112 may be an inflatable bladder, for example an air-inflatable bladder or bag, and a pump for changing an inflation level of the bladder, and a controller for controlling the pump. This provides a pneumatic actuation mechanism for controlling expansion and contraction of the article via inflation and deflation of the bladder. Thus action can provide the previously discussed first user-perceptible stimulus.

A hugging pillow is one example of a user friendly unit which could be used as the article 112 previously discussed. However, the above implementation is now limited to use of a hugging pillow. For example, other devices such as like handheld devices could be used. Furthermore, expansion/contraction is not essential as the first user-perceptible stimulus. Instead, other stimulation means could also be used, e.g. light, and/or sound etc.

By way of brief summary, features according to one particular implementation which is considered particularly advantageous by the inventors may include one or more of the following features:

a sleep induction apparatus (e.g. a pillow or cushion) with stimulus means for generating a paced first user-perceptible stimulation, e.g. an air bag or a mechanical inflation and deflation means.

one PPG sensor mounted on the surface of the pillow or cushion to sense a blood pulse through fingertips.

one finger belt or small bag to cover the PPG sensor on the hugging pillow for guiding stable finger positioning on the sensor.

a microcontroller or processing device to calculate and preferably monitor over time an HRV of the user, and to generate a real-time respiration curve of the user, according to the blood pulse signal, for use in tracking a phase of the user's respiration.

a same or different microcontroller or processing device to control generation of the paced stimulation, preferably for example by setting the pace of the stimulation at a frequency which stimulates a highest HRV (referred to above as the HRV resonant frequency).

Figure 18:
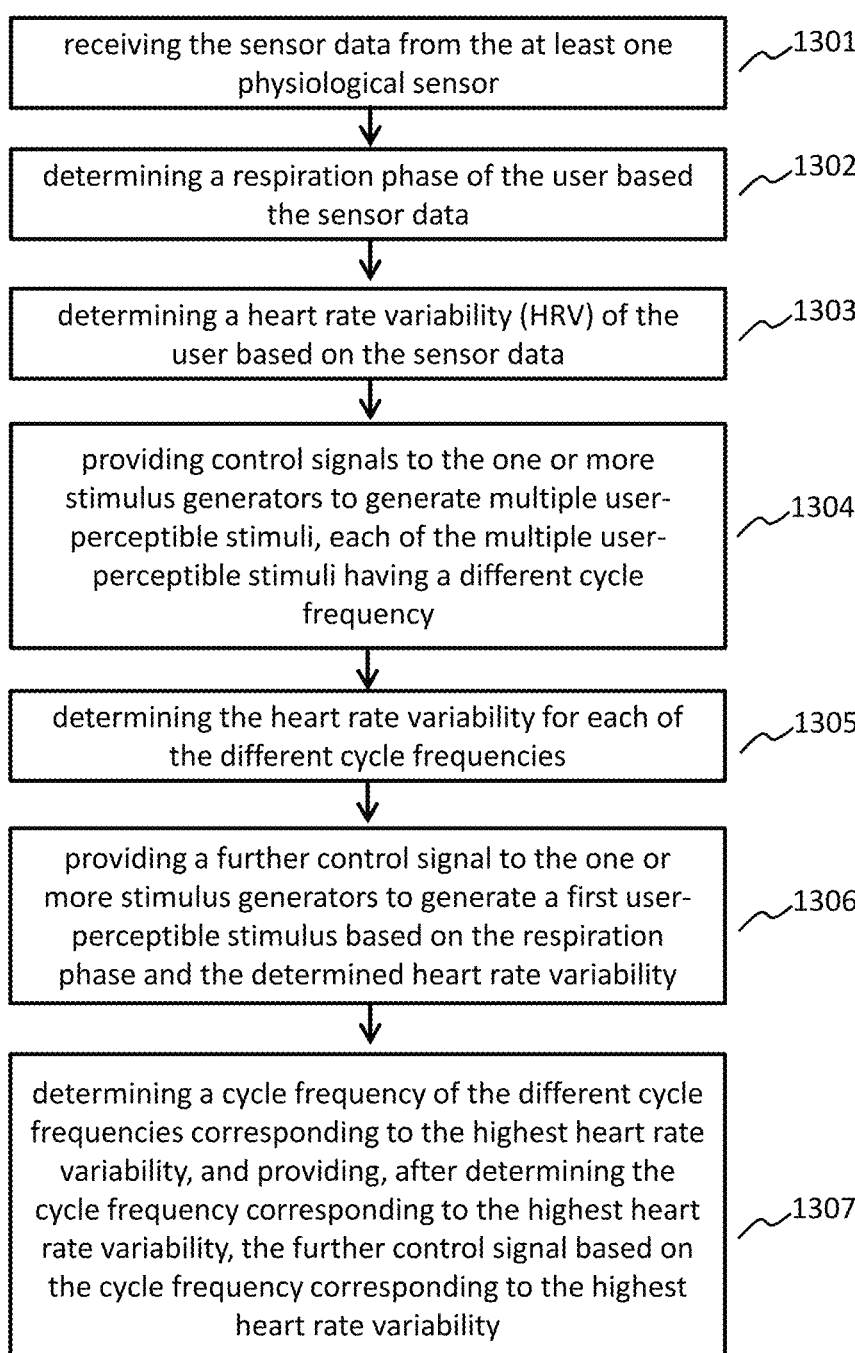
FIG. 18 outlines steps of a further example method in accordance with one or more embodiments of the invention.

FIG. 18 depicts a method according to an embodiment of the invention. The method is for controlling the sleep-aid apparatus 12. The sleep-aid apparatus 12 comprises one or more stimulus generators 42 operable to generate user-perceptible stimuli with one or more sensory modalities to guide the user 46 in matching a pacing of breathing of the user 46 to a cycle frequency of the user-perceptible stimulus. The sleep-aid apparatus 12 further comprising at least one physiological sensor 44 operable to generate sensor data. The method comprises steps 1301-1306. Step 1301 comprises receiving the sensor data from the at least one physiological sensor. Step 1302 comprises determining a respiration phase of the user based the sensor data. Step 1303 comprises determining a heart rate variability (HRV) of the user based on the sensor data. Step 1304 comprises providing control signals to the one or more stimulus generators to generate multiple user-perceptible stimuli, each of the multiple user-perceptible stimuli having a different cycle frequency. Step 1305 comprises determining the heart rate variability for each of the different cycle frequencies. Step 1306 comprises providing a further control signal to the one or more stimulus generators to generate a first user-perceptible stimulus based on the respiration phase and the determined heart rate variability.

The method optionally comprises step 1307 of determining a cycle frequency of the different cycle frequencies corresponding to the highest heart rate variability, and providing, after determining the cycle frequency corresponding to the highest heart rate variability, the further control signal based on the cycle frequency corresponding to the highest heart rate variability.

The method optionally comprises determining a synchronization status between a cycle phase of the first user-perceptible stimulus and the respiration phase of the user 46, and performing a response action based on the synchronization status, and wherein the response action comprises performing one or more adjustments of the cycle phase of the first user-perceptible stimulus so as to align with a current respiration phase of the user 46. The one or more adjustments are performed at recurrent/repeating time points.

The method optionally comprises determining a synchronization status between the cycle phase of the first user-perceptible stimulus and the respiration phase of the user 46, and performing a response action based on the synchronization status, and wherein the response action comprises providing a second control signal to at least one of the stimulus generators to generate of a second user-perceptible stimulus indicative of the synchronization status between the cycle phase of the first user-perceptible stimulus and the breathing phase of the user. The second user-perceptible stimulus comprises a stimulus which is continuously generated when the respiration phase of the user is synchronized with the cycle phase of the first user-perceptible stimulus; and not generated when the respiration phase of the user is non-synchronized with the cycle phase of the first user-perceptible stimulus.

The second user-perceptible stimulus optionally comprises a vibration stimulus. The method optionally comprises, when the respiration phase of the user is synchronized with the cycle phase of the first user-perceptible stimulus, modulating an amplitude of the vibration in synchrony with the respiration phase of the user.

In an embodiment, the sleep-aid apparatus 12 comprising one or more stimulus generators 42 operable to generate user-perceptible stimuli with one or more sensory modalities; at least one physiological sensor 44; and a processing device 36 adapted to perform the method of FIG. 18.

For example, the sleep-aid apparatus 12 comprises an article 112 for making physical contact with a user during sleep induction; and the physiological sensor 44 is integrated in the article 112. For example, the article is cushioned at least at a surface of the article. For example, the article is a pillow or a cushion.

In an embodiment, the at least one physiological sensor 44 is arranged so as to have a sensitive area accessible to physical contact at a surface of the article 112, and wherein said sensitive area is covered by a pocket or cover element 132 extending over the sensitive area, wherein the pocket or cover element 132 is attached to a surface of the article 112, and wherein the sensitive area is accessible to physical contact via an opening of the pocket or cover element 132. Optionally, the physiological sensor is a PPG sensor. Optionally, the first user-perceptible stimulus is a tactile or haptic stimulus and comprises a cyclical motion induced by an actuation mechanism.

In an embodiment, the invention is a computer program product comprising instructions which, when run on the processing device 36, cause the processing device 36 to perform the method according to the seventh aspect.

Any of the features described above in relation to any other embodiment may also be combined with the present set of embodiments. For example, a processing device may be provided as part of the sleep aid apparatus, and which is in accordance with any of the embodiments described above. The article 122 might be combined with any processing device already described above.

As mentioned previously, the invention can be embodied in software form. Thus another aspect of the invention is a computer program product comprising code means configured, when run on a processor, to cause the processor to perform a method in accordance with example or embodiment of the invention described in this document, or in accordance with any claim of this patent application.

Embodiments of the invention described above employ a processing device. The processing device may in general comprise a single processor or a plurality of processors. It may be located in a single containing device, structure or unit, or it may be distributed between a plurality of different devices, structures or units. Reference therefore to the processing device being adapted or configured to perform a particular step or task may correspond to that step or task being performed by any one or more of a plurality of processing components, either alone or in combination. The skilled person will understand how such a distributed processing arrangement can be implemented. The processing device may include a communication module or input/output for receiving data and outputting data to further components.

The one or more processors of the processing device can be implemented in numerous ways, with software and/or hardware, to perform the various functions required. A processor typically employs one or more microprocessors that may be programmed using software (e.g., microcode) to perform the required functions. The processor may be implemented as a combination of dedicated hardware to perform some functions and one or more programmed microprocessors and associated circuitry to perform other functions.

Examples of circuitry that may be employed in various embodiments of the present disclosure include, but are not limited to, conventional microprocessors, application specific integrated circuits (ASICs), and field-programmable gate arrays (FPGAs).

In various implementations, the processor may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality.

A single processor or other unit may fulfill the functions of several items recited in the claims.

The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

If the term "adapted to" is used in the claims or description, it is noted the term "adapted to" is intended to be equivalent to the term "configured to".

Any reference signs in the claims should not be construed as limiting the scope.

The invention claimed is:

1. A method for controlling a sleep-aid apparatus, the sleep aid apparatus comprising one or more stimulus generators operable to generate user-perceptible stimuli with one or more sensory modalities to guide a user in matching a pacing of breathing of the user to a cycle frequency of the user-perceptible stimulus, and the sleep aid apparatus further comprising at least one physiological sensor operable to generate sensor data, wherein the method comprises:

receiving the sensor data from the at least one physiological sensor;

determining a respiration phase of the user based the sensor data;

determining a heart rate variability (HRV) of the user based on the sensor data;

providing control signals to the one or more stimulus generators to generate multiple user-perceptible stimuli, each of the multiple user-perceptible stimuli having a different cycle frequency;

determining the heart rate variability for each of the different cycle frequencies;

providing a further control signal to the one or more stimulus generators to generate a first user-perceptible stimulus based on the respiration phase and the determined heart rate variability.

2. The method of claim 1, comprising determining a cycle frequency of the different cycle frequencies corresponding to the highest heart rate variability, providing, after determining the cycle frequency corresponding to the highest heart rate variability, the further control signal based on the cycle frequency corresponding to the highest heart rate variability.

3. The method of claim 1, comprising determining a synchronization status between a cycle phase of the first user-perceptible stimulus and the respiration phase of the user, and performing a response action based on the synchronization status, and wherein the response action comprises performing one or more adjustments of the cycle phase of the first user-perceptible stimulus so as to align with a current respiration phase of the user.

4. The method of claim 3, wherein the one or more adjustments are performed at recurrent/repeating time points.

5. The method of claim 1, comprising determining a synchronization status between the cycle phase of the first user-perceptible stimulus and the respiration phase of the user, and performing a response action based on the synchronization status, and wherein the response action comprises providing a second control signal to at least one of the stimulus generators to generate of a second user-perceptible stimulus indicative of the synchronization status between the cycle phase of the first user-perceptible stimulus and the breathing phase of the user.

6. The method of claim 5, wherein the second user-perceptible stimulus comprises a stimulus which is:

continuously generated when the respiration phase of the user is synchronized with the cycle phase of the first user-perceptible stimulus; and not generated when the respiration phase of the user is non-synchronized with the cycle phase of the first user-perceptible stimulus.

7. The method of claim 6, wherein the second user-perceptible stimulus comprises a vibration stimulus, and wherein the method comprises, when the respiration phase of the user is synchronized with the cycle phase of the first user-perceptible stimulus, modulating an amplitude of the vibration in synchrony with the respiration phase of the user.

8. A sleep-aid apparatus comprising:

one or more stimulus generators operable to generate user-perceptible stimuli with one or more sensory modalities;

at least one physiological sensor; and a processing device adapted to perform the method in accordance with claim 1.

9. The sleep-aid apparatus of claim 8, comprising an article for making physical contact with a user during sleep induction; and wherein the physiological sensor is integrated in the article.

10. The sleep-aid apparatus of claim 9, wherein the article is cushioned at least at a surface of the article.

11. The sleep-aid apparatus of claim 9, wherein the article is a pillow or a cushion.

12. The sleep-aid apparatus of claim 9, wherein the at least one physiological sensor is arranged so as to have a sensitive area accessible to physical contact at a surface of the article, and wherein said sensitive area is covered by a pocket or cover element extending over the sensitive area, wherein the pocket or cover element is attached to a surface of the article, and wherein the sensitive area is accessible to physical contact via an opening of the pocket or cover element.

13. The sleep-aid apparatus of claim 8, wherein the physiological sensor is a PPG sensor.

14. The sleep-aid apparatus of claim 8, wherein the first user-perceptible stimulus is a tactile or haptic stimulus and comprises a cyclical motion induced by an actuation mechanism.

15. A non-transitory computer readable medium storing instructions thereon which, when run on a processing device, cause the processing device to perform the method according to claim 1.

* * * * *